(12) United States Patent
Beckman

(10) Patent No.: US 12,226,275 B2
(45) Date of Patent: *Feb. 18, 2025

(54) ORAL CARE DEVICES HELD IN-MOUTH

(71) Applicant: Christopher V. Beckman, Los Angeles, CA (US)

(72) Inventor: Christopher V. Beckman, Los Angeles, CA (US)

( * ) Notice: Subject to any disclaimer, the term of this patent is extended or adjusted under 35 U.S.C. 154(b) by 555 days.

This patent is subject to a terminal disclaimer.

(21) Appl. No.: 17/517,646

(22) Filed: Nov. 2, 2021

(65) Prior Publication Data

US 2022/0054243 A1 Feb. 24, 2022

Related U.S. Application Data

(63) Continuation-in-part of application No. 16/533,757, filed on Aug. 6, 2019, now Pat. No. 11,160,362, which is a continuation-in-part of application No. 15/603,433, filed on May 23, 2017, now Pat. No. 10,368,632, which is a continuation-in-part of application No. 14/860,692, filed on Sep. 21, 2015, now Pat. No. 9,655,704, which is a
(Continued)

(51) Int. Cl.
| | |
|---|---|
| *A61C 17/22* | (2006.01) |
| *A46B 11/00* | (2006.01) |
| *A46B 15/00* | (2006.01) |
| *A61C 17/02* | (2006.01) |
| *A61C 17/20* | (2006.01) |
| *A61C 17/34* | (2006.01) |

(52) U.S. Cl.
CPC ........ *A61C 17/228* (2013.01); *A46B 11/0065* (2013.01); *A46B 15/0006* (2013.01); *A46B 15/0008* (2013.01); *A61C 17/0211* (2013.01); *A61C 17/20* (2013.01); *A61C 17/3481* (2013.01)

(58) Field of Classification Search
CPC ......... A61C 5/00; A61C 15/00; A61C 15/046; A46B 9/045; A46B 11/001; A46B 11/0041; A46B 11/0062; A46B 15/0004; A46B 13/023; A46B 13/04
See application file for complete search history.

(56) References Cited

U.S. PATENT DOCUMENTS

| | | | |
|---|---|---|---|
| 6,893,259 B1 * | 5/2005 | Reizenson | A61C 17/0211 433/29 |
| 8,978,189 B1 * | 3/2015 | Sexton | A46B 9/045 15/28 |

(Continued)

*Primary Examiner* — Shay Karls

(57) ABSTRACT

Hands-free systems, devices and methods, adapted for brushing, cleaning and treating all of a user's teeth simultaneously, are provided. In some embodiments, such a device comprises brushes for cleaning all of a user's teeth simultaneously. In some embodiments, such a device includes a generally U-shaped channel(s), accepting, cleaning and/or treating all of a user's teeth simultaneously. Customized fluid jets within such devices are provided, introducing dentifrices and other treatments into the channels. In some embodiments, compartments and cartridges with a proprietary form factor for delivering dentifrice and other treatments and for disposing of waste without mess are provided. In some embodiments, data are gathered, analyzed and serve as the basis for a treatment plan, which may then be carried out by the system(s), device(s) and method(s), over time.

20 Claims, 16 Drawing Sheets

Related U.S. Application Data continuation-in-part of application No. 13/570,241, filed on Aug. 8, 2012, now Pat. No. 9,138,304.

(56) References Cited

U.S. PATENT DOCUMENTS

| | | | |
|---|---|---|---|
| 11,160,362 B2* | 11/2021 | Beckman | A61C 17/20 |
| 2009/0208898 A1* | 8/2009 | Kaplan | A46B 9/045 433/80 |
| 2015/0282910 A1* | 10/2015 | Furdui-Carr | A46B 9/045 15/22.1 |

* cited by examiner

ORAL CARE DEVICES HELD IN-MOUTH

CROSS-REFERENCE TO RELATED APPLICATION

This application is a continuation of U.S. patent application Ser. No. 16/533,757, filed Aug. 6, 2019, entitled "All-at-Once, Teeth-Surrounding, Oral Cleaning Device and Methods," now U.S. Pat. No. 11,160,362, which is a continuation-in-part of U.S. patent application Ser. No. 15/603,433, filed May 23, 2017, entitled "Simultaneous Flossing and Brushing Device," now U.S. Pat. No. 10,368,632, which is a continuation-in-part of U.S. patent application Ser. No. 14/860,692, filed Sep. 21, 2015, entitled "Bite-Activated Dental Hygiene Device," now U.S. Pat. No. 9,655,704, which is a continuation-in-part of U.S. patent application Ser. No. 13/570,241, filed Aug. 8, 2012, entitled "Bite-Actuated Tooth Cleaning Techniques," now U.S. Pat. No. 9,138,304. The entire contents of each of the above applications are hereby incorporated by reference into the present application as if fully set forth herein.

FIELD OF THE INVENTION

The present invention relates to the fields of teeth-cleaning and other oral cavity cleaning devices and dentifrices.

BACKGROUND

Although the modern toothbrush did not spread throughout Europe until the 1600s, teeth- and gum-cleaning implements have been in use for many centuries, and date before recorded history. Typically, in the modern era, a toothbrush includes a handle connected to a set of round-ended, flexible bristles, and is used with toothpaste or other dentifrice and water to clean teeth and gums. In the United States, toothpastes usually include a soap for cleaning and a fluoride compound, for its anti-cavity and pro-mineralization properties to protect teeth from decay. Toothpaste is usually not ingested, and may be poisonous to ingest, but some "natural ingredients," such as enzymatic and other toothpaste alternatives, have been developed that may be safer for animals to ingest. Although the safety and efficacy of many specific dentifrices may be debated, the overall health and hygiene benefits of brushing teeth with a toothbrush and a dentifrice is widely accepted and is part of the ordinary routine of a vast majority of people in the most developed countries.

It should be understood that the disclosures in this application related to the background of the invention, in, but not limited to this section titled "Background," do not necessarily set forth prior art or other known aspects exclusively, and may instead include art that was invented concurrently or after the present invention and conception, and details of the inventor's own discoveries and work and work results.

SUMMARY OF THE INVENTION

New oral care devices and methods are provided. In some embodiments, portable, hands-free devices adapted for brushing, cleaning and/or treating users' teeth, gums and oral cavity are provided. In some embodiments, such a device comprises brushes for cleaning each of a user's teeth simultaneously. In some embodiments, such a device is generally U-shaped, with channels lined with such brushes, and configured for accepting, cleaning and/or treating all of a user's teeth simultaneously.

In some embodiments, such a device is adapted to fit an individual user, based on molds, impressions or other 3-dimensional imaging or information techniques, allowing for more effective, thorough brushing experiences.

In some embodiments, example customized washing ports, comprising a wide variety of example dental and interdental materials, such as oral treatment and cleansing products, are set forth. In some such embodiments, such customized washing ports are jets configured to expelling a cleaning or treatment fluid. In some such embodiments, the jets expel such a fluid in lines for flossing a user's teeth. In some embodiments, the jets expel such a fluid toward a gum line of a user, to remove material and treat the user's gums and teeth at the gum line.

In some embodiments, specialized handles for oral care devices are set forth, configured for maintaining access to controls while leaving such a device in place in a user's mouth during cleaning and treatment, hands-free. In some such embodiments, such controls issue commands to a control system, which may be comprised in, or partially comprised in, the oral care device. Many example methods, modes and durations for many such devices' use are also set forth, including, but not limited to: a rapid brushing mode, a travel brushing mode, a deep-cleaning mode, a whitening mode and various other teeth-, gum- and oral cavity-treatment and -cleaning modes. In some embodiments, the control system controls the vibrations, strokes, intensity of brushing and, strength, amount and direction of fluid from jets, an amount of dentifrice or treatment material introduced to user's teeth or mouth, and parts thereof, and any other aspect of the device's actuation, which may be in accordance with a mode(s) or duration(s) of actuation and use.

In some embodiments, customized compartments and cartridges with a proprietary form factor are provided. In some embodiments, such cartridges are installed and uninstalled in a loading compartment of such devices, where they are connected via ports for delivering dentifrice and other treatments. In some embodiments, such a device and/or cartridge is disposable and/or recyclable, and configured for receiving and disposing of waste without mess. In some embodiments, observational data are gathered, analyzed and serve as the basis for a cleaning and/or treatment action plan.

Such an action plan may include treatment parameters governing cleaning and treatment mode(s) and duration(s), and observations, recommendations and feedback provided to be provided to users, in some embodiments. For example, in some embodiments, the action plan may include a series of cleansing and/or treatment cartridges, to be used according to instructions, and in modes and durations designated. In some embodiments, such an action plan, and any and all treatments or cleansing, may be executed with the assistance of a control system, included, or partially included, in the oral care device, as discussed above.

In some aspects of the invention, an implement with bite-actuated tooth cleaning aspects known and branded as a CLEANCHEW™ is provided, which may comprise tooth and gum brushing protrusion and/or bite-guided channel opening pairings or sets, which channel pairings or sets may include features, projections and/or spacers and one-way valves to permit the biting-actuated release of dentifrice from an inner chamber. In further aspects of the invention, internal springs and the tension of surrounding material aid in creating bite actuation. In still other aspects of the invention, movable bite-actuated and/or motor-actuated members conform an elastomeric or flexible outer layer with additional sub-features that aid in teeth and oral cavity cleaning.

In other embodiments, an interstitial fluid, gel or other medium, which may or may not be present in a separate interstitial layer defined by a lining, and which may or may not include a dentifrice and may or may not change its viscosity, hardness and other properties upon contact with air, aids in enabling re-sealing an inner chamber following penetration of the CLEANCHEW. Outside of that interstitial layer, an additional interstitial layer containing a gas, fluid or other agent that hardens or congeals with or causes to harden or congeal, the interstitial fluid, gel or other medium within the interstitial layer, may be included and, preferably, is comprised of chambers, locks or angled channels that maintain coverage, pressure and/or mixing between the fluids, gels or other media of the two interstitial layers at the point of perforation of a mutual wall, despite a perforation of other walls of the layers. This aspect may also be applied to a variety of other related arts, including but not limited to pneumatic and other tires, to aid in remediating fluid leaks from piercing or other deformation of a pneumatic tire structure. For example, in the instance of a tire, a chamber above each possible point of perforation may have a gradual drain in its wall at a point just above the possible point of perforation, allowing the slow dousing of the perforation with the combined-hardening component in the outer interstitial layer. The fluid, gel or other medium in the outer interstitial layer may also have a signal dye to indicate that the tire has been compromised, while maintaining pressure due to the resulting seal from hardening or congealing by mixing of the two layers of fluid, gel or other medium.

Unless otherwise indicated, the following terms have the specific meaning described herein:

A "CLEANCHEW," in addition to its ordinary meaning and special meaning in the art to which it pertains, means each of the following aspects, both alone and in each possible combination, as if separately set forth: an object, preferably comprising an elastomeric or other pliant, flexible or rebounding solid material, that may be chewed and/or bitten by an animal and, due to such chewing and/or biting either or both: (1) releases a fluid, gel, liquid and/or dentifrice from a contained cavity or other feature of the CLEANCHEW in the direction of outer or scrubbing features of the CLEANCHEW or of the teeth or other oral cavity features of the animal; and/or (2) leads to and/or actuates scrubbing or cleaning by protrusions or other features on the outer surface of the object. In addition or alternatively, a CLEANCHEW may comprise a refillable inner chamber(s) variably containing dentifrice and/or any animal-bitable object that may aid in the animal's oral hygiene.

DETAILED DESCRIPTION OF THE INVENTION

Figure 1:
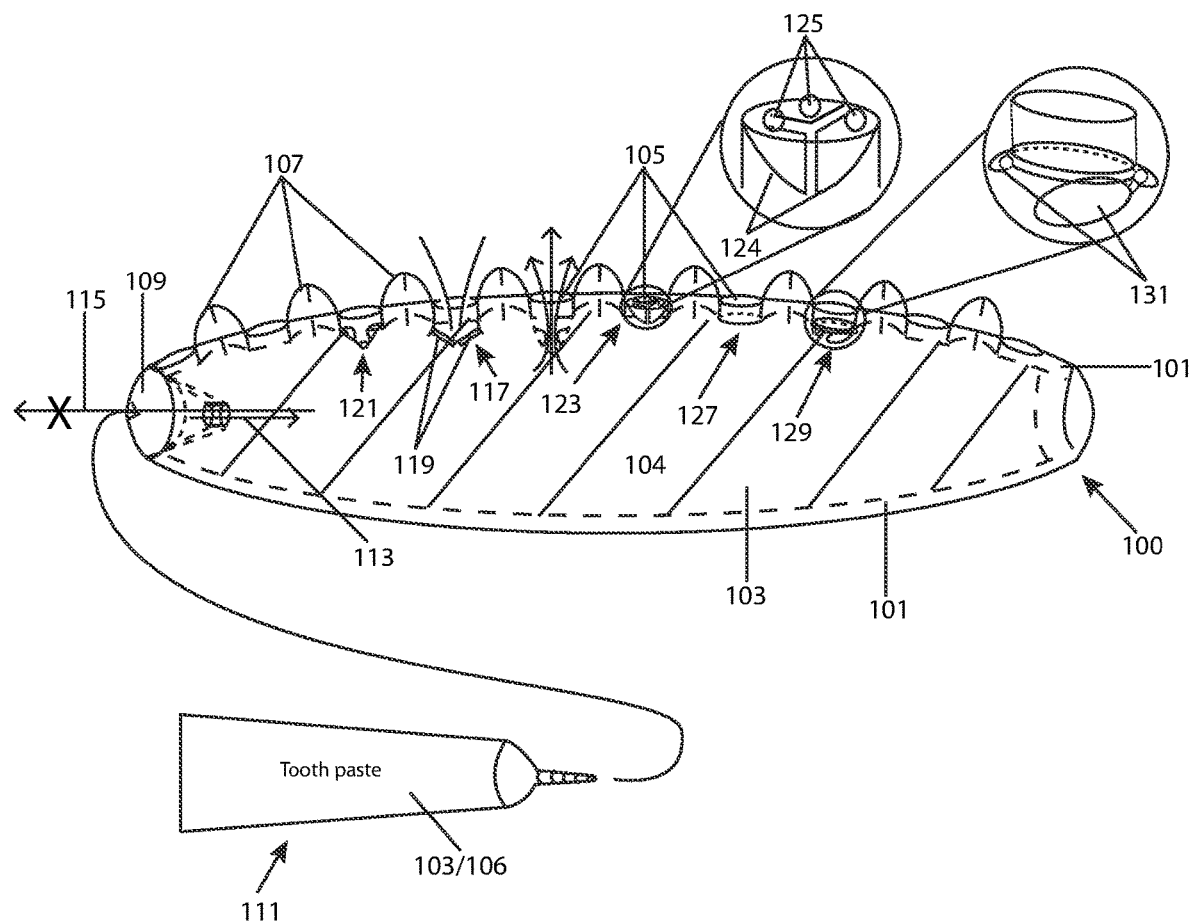
FIG. 1 is a partial illustration of some components of a CLEANCHEW and incorporated dentifrice, in accordance with aspects of the present invention.

FIG. 1 is a side-view illustration of a CLEANCHEW bite-actuated cleaning system 100 for mammalian pets. The entire CLEANCHEW is designed to be safely bitten by a typical mammalian pet, and preferably is small enough that a pet's jaws may encompass at least its narrowest widths and, as a result, dispense dentifrice and actuate a scrubbing action to aid in cleaning teeth and the oral cavity of the pet generally. A flexibly, compressible and expandable outer containing layer 101 contains a dentifrice or other cleaning liquid, fluid or gel ("fluid") 103 in a cavity 104, which is variably dispensable to assist in cleaning the oral cavity of a pet, preferably, a mammalian pet. As will be explained in greater detail below, fluid 103 may be dispensed to the oral cavity of a mammalian pet by biting action, via bite-dispensing, cleaning-featured openings, such as those examples shown as 105, that are designed to accept variably-sized biting teeth. In addition, projections and/or textures, such as projections 107, provide natural abrasion, massage, polishing and/or scrubbing, also driven by biting action. A refilling port 109 permits the filling or refilling of cavity 104 from a complementarily-shaped intermediate fluid storage container 111, which may contain additional or differing fluid 103 and/or 106 such as, as its label is pictured to indicate, toothpaste. Preferably, port 109 is round, cylindrical or conical or otherwise has radial symmetry and comprises a one-way fluid valve, permitting the influx of fluid as shown by fluid motion arrow 113, but which prevents outward flow of fluid, out of cavity 104 through port 109, as shown by stricken fluid arrow 115.

FIG. 1 illustrates a variety of possible exemplary cleaning-featured openings. For example, opening 117 is an exemplary one-way valve opening, with elastomeric variably cavity enclosing features 119. In a resting state, features 119 converge with one another and prevent the outward flow of fluid from cavity 104. However, if a tooth, such as a mammalian tooth, enters opening 117 deeply enough, or with sufficient lateral pressure against them or surrounding, attached material, features 119 may be pulled or pushed away from one another, permitting the outward flow of fluid. Preferably, the overall design of cleaning featured openings, such as 117, alone or in combination with surrounding material shapes and properties, tends to channel teeth and other biting projections that are pressed against CLEANCHEW 100 substantially into the center of the openings. Another preferred form of cleaning-featured opening is shown as opening 121, and will be discussed in greater detail with reference to FIG. 2.

Another preferred form of cleaning-featured opening is shown as 123, which has a tricuspid one-way valve opening, with three semi-flexible flaps 124 to prevent escape of liquid, fluid or gel 103, unless and until a member, such as a tooth, pushes them away from one another (open) with the aid of optional tooth-action-facing, complementarily-shaped push members 125. 123 is shown in enhanced detail by a second rendering in a zoomed in window in FIG. 1.

Another preferred form of cleaning-featured opening is shown as 127, which comprises a sealing membrane 128 that may be pierced by animal biting and which may be scored to then create flaps that still resist the flow of liquid, fluid or gel 103 out of the CLEANCHEW to some degree, but that then permit 103 to flow onto the teeth and gums of the biting animal. An additional stop-cock or gravity ball valve (such as those used for animal water dispensers, and which close when pointed downward, at the gravitational bottom of the CLEANCHEW, may aid in preventing gravitational draining of the CLEANCHEW.

Another preferred form of cleaning-featured opening is shown as 129, with a zoom window to enhance detail, which comprises multiple hinged or flexible attached leaves 131, each of which, by itself, if driven by outward-flowing liquid, fluid or gel 103, substantially close opening 129, but any or all of which may again be forced open by a biting action or tooth.

Although a limited group of cleaning-featured openings and projections are shown at the top of the CLEANCHEW shown in FIG. 1, it should be understood that such cleaning-featured openings, projections and other cleaning textures and aspects disclosed in this application may cover substantially all bite or oral interfacing surfaces of a CLEANCHEW, or select regions better positioned to affect cleaning of an oral cavity or other cavity of an animal.

Figure 2:
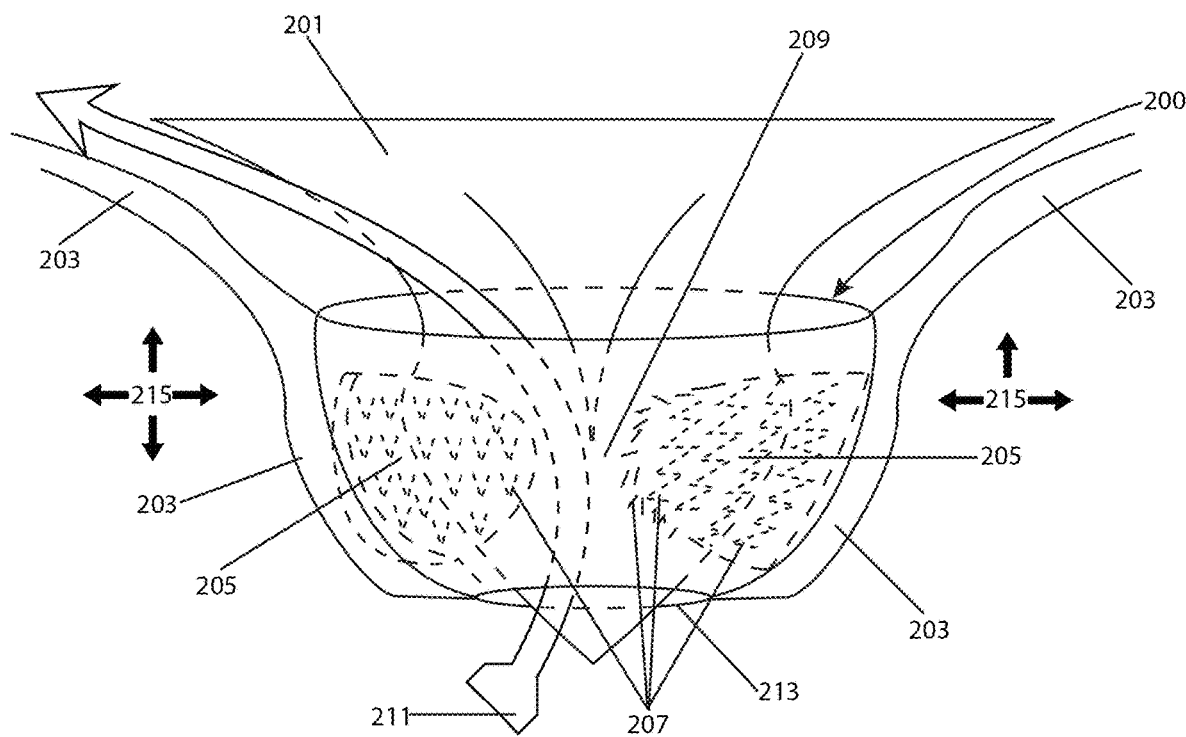
FIG. 2 is a side perspective view of an example cleaning-featured opening, in an outer fluid containing layer of a CLEANCHEW, such as the CLEANCHEW shown in FIG. 1.

FIG. 2 is a side perspective view of an exemplary cleaning-featured opening 200, in an outer fluid containing layer of a CLEANCHEW, such as the CLEANCHEW shown in FIG. 1. A mammalian tooth 201 has substantially entered opening 200 due to a biting action of the mammal into and/or against the outer layer of the CLEANCHEW of which it is a part. The outer layer of the CLEANCHEW in which both the cleaning featured opening 200 and the tooth 201 are embedded, is partially shown as 203. Lining the outer surface of cleaning-featured opening 200 are scrubbing surface features 205, which preferably comprise and are at least partially surface-covered by scrubbing and fluid-absorbing projections, such as the projections shown as 207. As the mammal bites, and tooth 201 enters opening 200, projections 207 drag and/or rub against tooth 201, aided by surface tension of the outer surfaces of opening 200, and thereby scrub the surface of tooth 201. Features 205 and/or projections 207 preferably do not cover the entire outer surface of opening 200, and therefore abut surface gaps between them such as that shown as 209. As a result, when a tooth has penetrated opening 200, features 205 and projections 207 further serve as towers which vault the outer surface of opening 200 between them, and temporarily (as long as the tooth remains embedded in opening 200) permit the outward flow of fluid through the resulting volumetric gap, as shown, for example, by fluid motion arrow 211.

An inside port 213 of opening 200 is, when in the CLEANCHEW is in a resting state, substantially closed, and prevents the outward flow of material via elastomeric properties of the material comprised by the opening. However, when a tooth, such as tooth 201, enters opening 200, and therefore stretches its outer surface, port 213 may be pulled open due to the semi-flexible, semi-rigid nature of the material comprised in the outer layer and/or its surface, temporarily permitting the outward flow of fluid contained in cavity 215.

Figure 3:
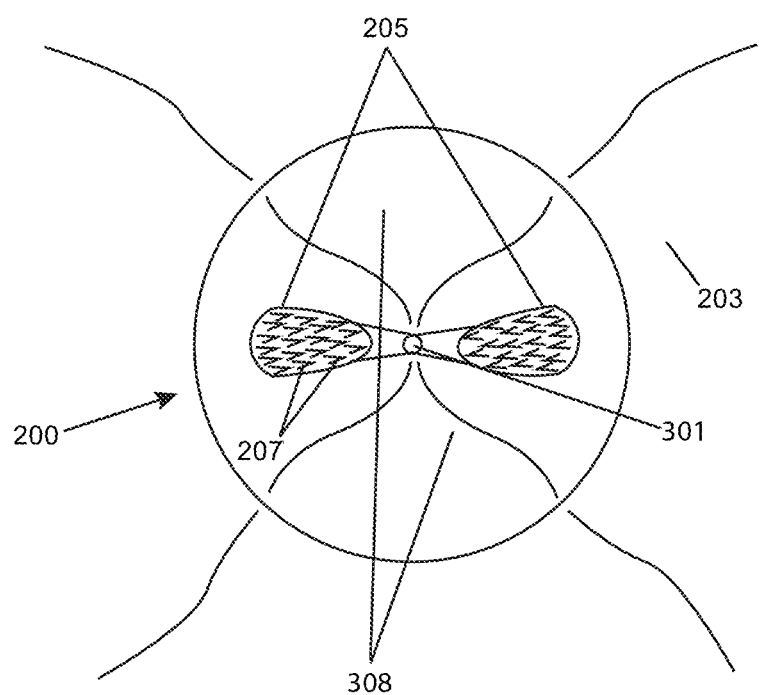
FIG. 3 is a top view of the same example cleaning-featured variable opening as that depicted in FIG. 2, and serves to illustrate further embodiments of the present invention.

FIG. 3 is a top view of the same cleaning-featured variable opening 200 pictured in FIG. 2, and serves to illustrate further exemplary aspects of the present invention. In the instance of FIG. 3, a tooth is not shown penetrating opening 200 and, as a result, the inside port, now shown as 301, is substantially closed in its undisturbed, resting conformation, preventing the outward flow (which would correspond with upward, out-of-the-page or positive z-axis flow in the figure) of fluid from the fluid containing side of layer 203, in which cleaning-featured opening 200 is embedded. In this resting conformational state, scrubbing features, such as 205, and projections, such as 207, may be seen in an unobstructed top view, and are contracted into a position substantially tighter (with less space between them) than the volume that would be occupied by a tooth if sufficiently embedded into the opening 200 and between them, which would therefore create tension that could be used for scrubbing against any such tooth. Tooth-guiding channels, exemplary edges of which are shown as 308, are also illustrated more clearly from the top-view, and extend beyond the depression in containing layer 203 comprised by opening 200, illustrating how, regardless of where a tooth happens to land on the surface of a CLEANCHEW, it may be guided into a cleaning-featured opening, such as that featured as 200. Of course, a wide variety of alternate channeling feature shapes may be used, aside from those partially illustrated as sloping downward (into the page of the figure) and towards the center of port 301 in a parabolic or otherwise curved shape, as shown in FIG. 3. Such alternate channeling feature shapes may also comprise abrading or scrubbing sub-features, which, as with other scrubbing features discussed with respect to other figures, may be angled such that their edges better catch the edges of debris and tartar from one, two, more or opposing directions of tooth movement. As such, configurations of such sub-features may be used that are effective regardless of whether a tooth is moving inward or outward (e.g., due to biting, or opening) and/or twisting and scrubbing or brushing can be more efficient.

Figure 4:
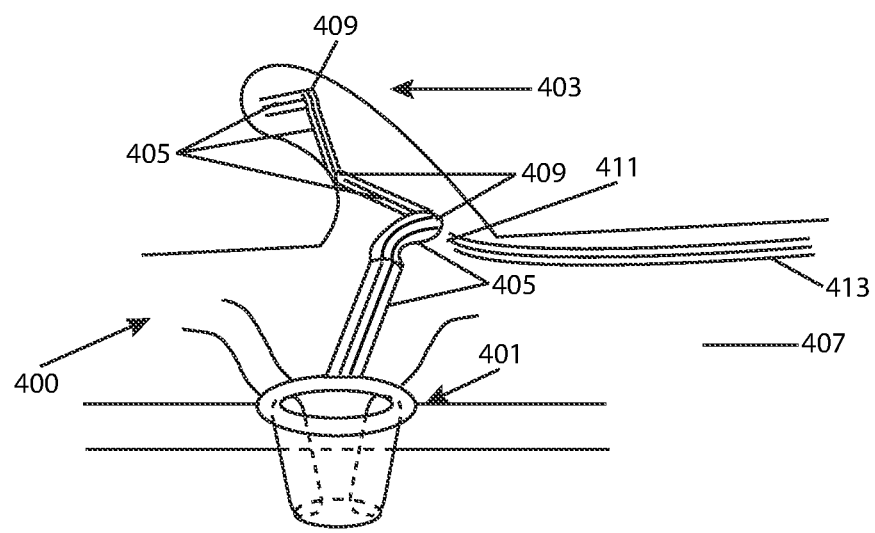
FIG. 4 is a side perspective view of an example cleaning-featured variable opening and bite-induced shifting outward projection combination unit—specifically, a pairing—in its resting conformational structure, prior to biting or tooth penetration of a CLEANCHEW comprising the pairing.

FIG. 4 is a side perspective view of an exemplary cleaning-featured variable opening and bite-induced-shifting scrubbing outward projection combination unit—specifically, a pairing—in its resting conformational structure, prior to biting or tooth penetration of a CLEANCHEW comprising the pairing. In the pairing 400, a cleaning-featured variable opening 401 (for example, such openings of any style discussed elsewhere in this application or as illustrated in FIG. 4), is united with a scrubbing outward projection 403 (again, for example, such projections of any style discussed elsewhere in this application or as illustrated in FIG. 4) and is so united by connecting intermediate material, comprising a banded spring element(s) 405, which has/have both (1) resting and (2) biting-actuated conformational structures, which lead to different resting and biting-actuated conformational structures in surrounding attached flexible layer(s) or surface materials 407, which is, preferably, an elastomeric material or fabric and in which spring element(s) 405 are embedded and/or connected. Spring element(s) 405 are shown in its/their resting conformational state, meaning that the CLEANCHEW comprising it/them is not currently being bitten, or, at least not in or about the location of the pairing 400. In this state, the resting surface tension of surrounding material 407 may lead spring element(s) 405 to be compressed, as by non-deformational bends and/or compressions 409. In addition, tension-reducing or -breaking bend 411 may variably separate or reduce connections or spring aspects in neighboring material, such as neighboring spring element(s) 413 from spring element(s) 405. In this state, that resting surface tension and/or the resting conformational state of spring element(s) 405 and 413 and their variable connections, may lead projection 403 to be in a curved, leftward facing structural state. However, as will be discussed in greater detail with respect to FIG. 5, when bitten, chewed or otherwise physically insulted, alternate conformational states due to changes in surface tension may lead projection 403 to move into a different structural position, and resultantly brush teeth, gums and/or other oral cavity aspects that the projection may be in contact with. As suggested above, a pairing of one exemplary cleaning-featured variable opening and one bite-induced shifting scrubbing outward projection is exemplary only, and triplets, quartets and much more complex interacting physical relationships between variable openings and bite-induced shifting scrubbing outward projections and/or comprised or related spring elements may be, alternatively, used in accordance with aspects of the present invention, including, but not limited to, relationships where bite-driving of more distant openings, or other differently spaced openings, lead to different conformational results for projections that are more likely to effectively brush a surface area of a pet's mouth at that distance. For example, spring bands aligning (actuated conformation) with more distant openings only may lead to brushing in directions conforming with the roof of a mouth, rather than, for example, a curved massaging actuation motion which may be created closer to tooth gums.

Figure 5:
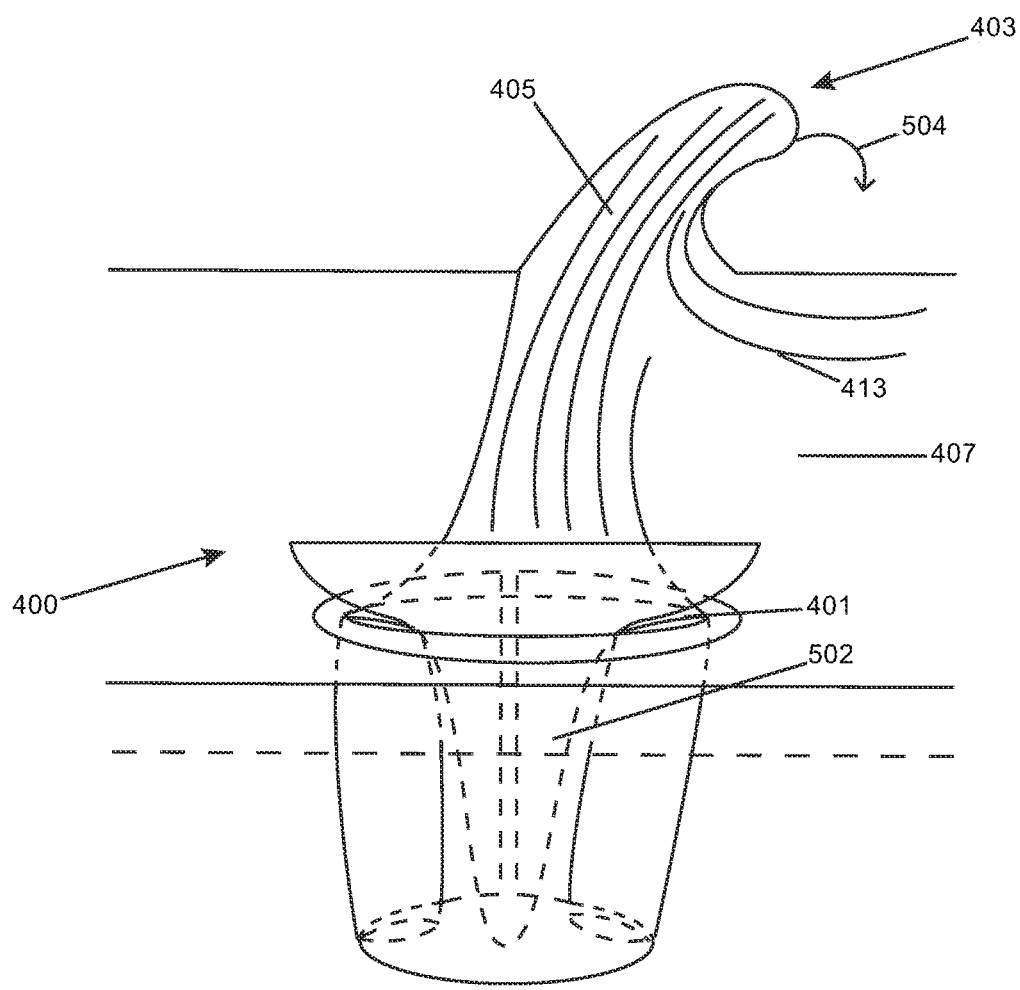
FIG. 5 is another view, from the same perspective, of the same example pairing as that illustrated in FIG. 4, but in another conformation resulting from biting and tooth penetration of the pairing.

FIG. 5 is another view, from the same perspective except that some aspects have been enlarged, of the same exemplary pairing 400, as that illustrated in FIG. 4, but in another structural conformation resulting from biting and tooth penetration of the variable opening 401 of the pairing. Thus, in FIG. 5, a tooth 502 is illustrated as inserted into variable opening 401, creating both downward and outward pressure on opening 401 and creating surface tension in surface materials 407. More specifically, that pressure tends to align banded spring elements 405, to remove conformational folds. More straightened and aligned elements 405 and 413 then approach and achieve a conformational state in which folds disappear and the elements apply a rightward, curving motion in the scrubbing outward projection 403. That motion is illustrated by motion arrow 504, and may aid in scrubbing gums and neighboring teeth.

Spring element(s) 405 preferably have multiple stable resting conformations that may be switched by biting or other interaction with the surface of the CLEANCHEW. In addition, although this application has stressed biting-actuation for causing a shift from and to resting stable or other conformations of spring elements 405, and driving scrubbing projections and features, it should be noted that such spring elements may instead, or in addition, drive dilation and contraction of CLEANCHEW surface variable openings such that, when a projection or other surface feature is sufficiently bent over or pulled sideways or compressed by rubbing against a surface to be cleaned, then and only then are spring elements aligned that cause outward, opening tension on the rims and surfaces of fluid, gel and/or liquid-containing orifices. Also preferably, intermediate fluid, gel and/or liquid-containing antechamber(s), preferably abutting, variably opening into and smaller than a main fluid, gel and/or liquid-containing cavity, and also abutting and sharing the variable opening(s) to the surface of the CLEANCHEW, receive such fluid, gel and/or liquid from the main cavity only by a variable valve which substantially closes during a sufficient scrubbing action that drives surface features sufficiently to cause the spring elements to drive dilation of CLEANCHEW surface variable openings. It should also be noted that, although separate spring elements and outer CLEANCHEW layer materials are discussed, a single material, with spring properties and resting conformational state(s) may instead be used as both the material layer and spring element(s), such that surface deformation or teeth acceptance may drive variable opening of both a main fluid, gel and/or liquid-containing chamber, and/or intermediate antechambers, into CLEANCHEW surface variable openings.

Figure 6:
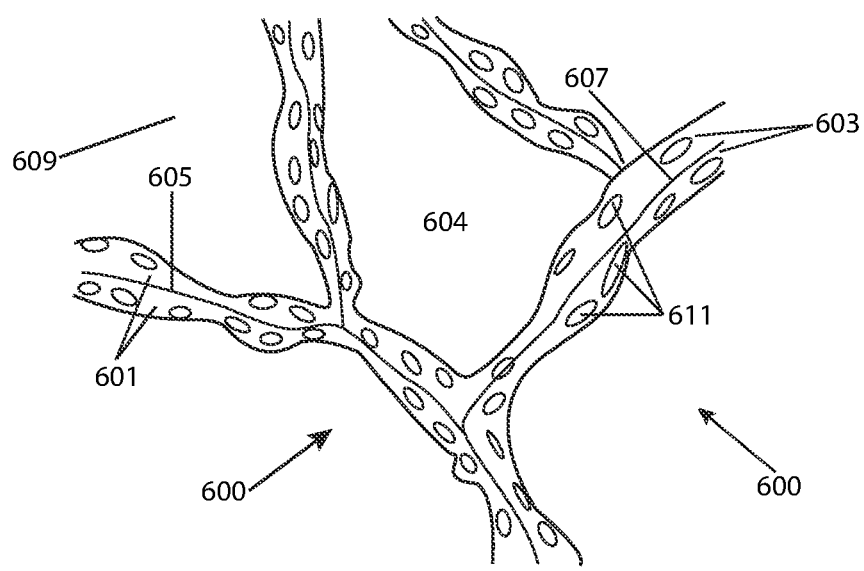
FIG. 6 is a partial top-view of example bitable surface features of a CLEANCHEW, in accordance with additional aspects of the present invention.

FIG. 6 is a partial top-view of exemplary bitable surface features of a CLEANCHEW, in accordance with additional aspects of the present invention. Reticulated or interspersed grooves, such as those depicted as 600, comprise converging channel sides, such as those shown as converging channel side pairings 601 and 603. Such converging channel sides are within an outer CLEANCHEW material layer the outer surface of which is labeled 604, and may, when a tooth penetrates between where converging channel sides meet (such as that shown as convergences 605 and 607) separate sufficiently to permit a fluid from a contained cavity to flow outward (toward the viewer of the figure), and toward the penetrating tooth and gums in which the tooth may be embedded. The meeting points of the converging channel sides are more distant from the viewer of the picture than the main surface 609 of the outer layer of the CLEANCHEW—meaning that as converging side pairs such as 601 and 603 converge, to extend the example, at convergences 605 and 607, respectively, their surfaces slope inward, into the page, away from the viewer of the figure as they slope toward their convergences. Lining the outer surface of converging side pairings, such as 601 and 603, are scrubbing surface features, such as those shown as 611, which preferably comprise and are at least partially surface-covered by scrubbing and fluid absorbing projections, such as those discussed elsewhere in this application, and all of such features facilitate both scrubbing and the creation of temporary fluid-escape gaps during animal biting of the CLEANCHEW.

Figure 7:
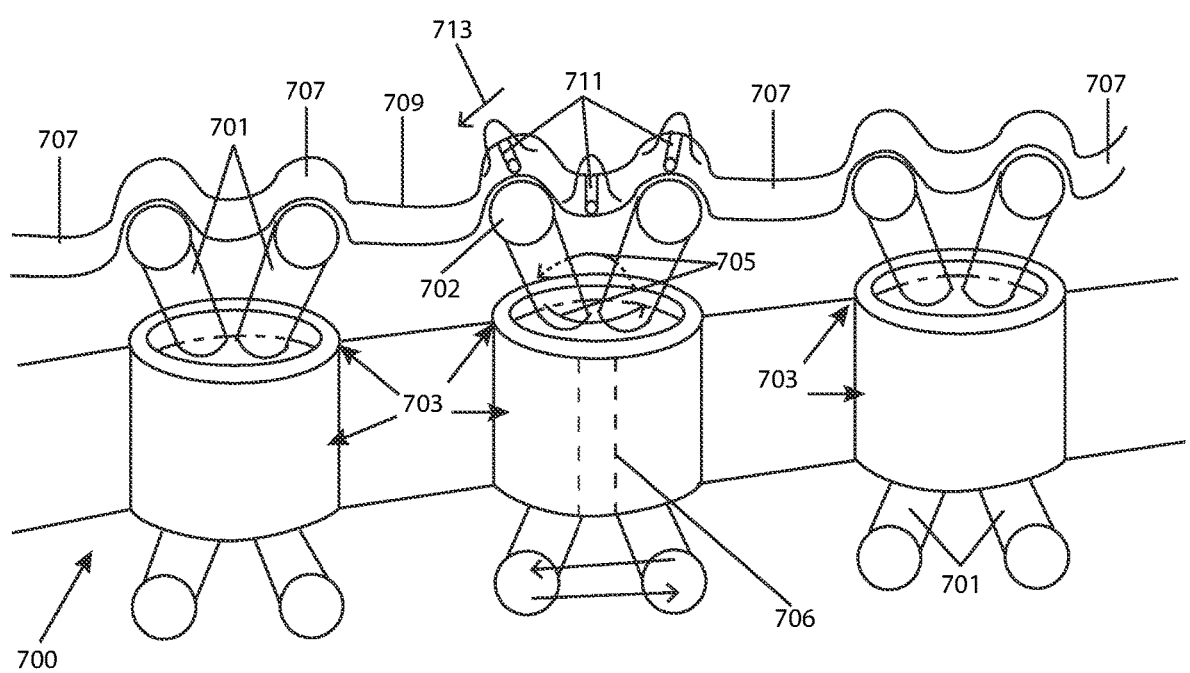
FIG. 7 is a side-view of part of an example CLEANCHEW that includes biting- and/or motor-actuable movable structural members.

FIG. 7 is a side-view of aspects of a CLEANCHEW 700 that comprises biting- and/or motor-actuable movable structural members. Major biting- and/or motor-actuable movable structural members, such as those shown as examples 701, and which are generally cylindrical but with semi-spherical tops such as that shown as 702, extend from and are mounted to movable ball-and-socket, turret or swivel joints 703, about which they may rotate, as shown by exemplary rotational motion arrows 705 in the instance of a swivel joint (swiveling around a circular rotation axel, such as axel 706), or those major members may rotate in any spherical direction, in the instance of a ball-and-socket or turret joint. Major members 701 are buried beneath outer CLEANCHEW containing layer 707 (layer 707 being shown in vertical cross-section to avoid blocking the view of other aspects of the invention), which is preferably made of an elastomeric or flexible yet deformation-resistant material. Preferably, layer 707 is stretched over major members such as 701 with sufficient tension that the members are in contact with and variably shape (with their motion within joints 703) the surface layer 707. Such contact also aids in permitting biting on the outer surface of the layer 709 to drive motion of the major members such as 701. But, optionally or in addition, joints 703 may also be driven by servo/motors. Either way, the resulting moving surface shapes of layer 707 result in scrubbing and massaging of gums and teeth of an animal biting into layer 707 with its teeth. Minor biting- and/or motor-actuable movable structural members, such as the examples shown as 711, are preferably smaller than major members 701, and may be embedded in layer 707, and may move both in reaction to the same animal biting (which, as discussed above, may drive the motion of major members 701), and in reaction to motion of the major members, which may push minor members 711 upward and/or downward and/or rotate them about lever rotational axes. Minor member 711, therefore, are or create motion-variable scrubbing/massaging sub-features in layer 707, in which they are embedded. For example, if major members 701 move as shown in the second joint from the left of the illustration by motion arrows 705, the top of the left-most minor member may move into the page and to the left, in reaction, as shown by motion arrow 713.

Figure 8:
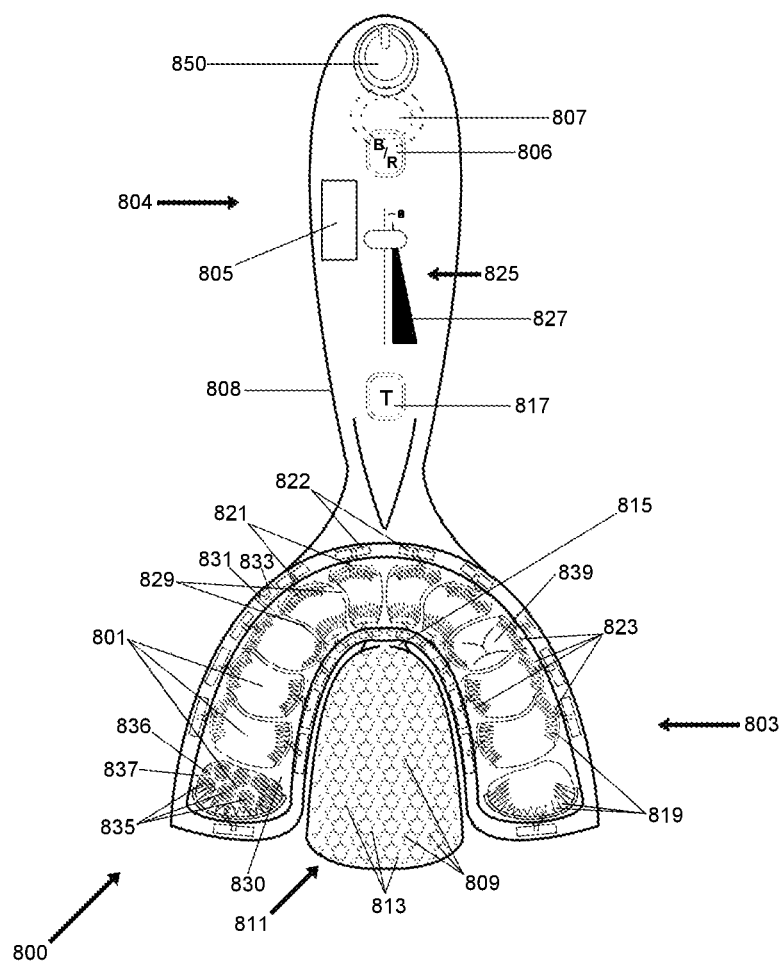
FIG. 8 is a top view of an example oral care device for cleaning the teeth and oral cavity of a mammalian animal.

FIG. 8 is a top view of an example oral care device 800, for cleaning the teeth and oral cavity of a mammalian animal. More specifically, oral care device 800 is custom-fitted to accommodate the teeth and/or at least part of an oral cavity of a human user (not pictured), and may be actuated by placement or a single bite by the user causing the user's teeth to enter teeth-accepting and -scrubbing channels, such as the example upper channel 801, of device 800. It should be understood that, due to the perspective of the figure, only an upper channel 801, shaped to fit and accept a user's upper row of teeth, is visible in FIG. 8, but, at least in some embodiments, at least another, lower, second channel is also included in oral care device 800, such as a channel shaped to fit and accept a user's lower row of teeth. In such embodiments, such a lower second channel may include any of the aspects set forth below, with respect to upper channel 801. In some embodiments, as with other oral care devices set forth in the present application, oral care device 800 and upper channel 801, in addition to scrubbing, or alternatively thereto, aid in the treatment of a user's teeth (e.g., by administering teeth-strengthening and/or enhancing substances). In some embodiments, oral care device 800 aids in the cleansing, treatment and/or other enhancement of a user's tongue, oral cavity and/or oropharynx (e.g., by administering soaps, antiseptics, antiseptics, vitamins, minerals, protectants, beneficial organisms and/or antibiotics).

Generally speaking, oral care device 800 comprises an example cleaning head end 803 and an example handle grip end 804. By holding handle grip end 804, a user of oral care device 800 may insert cleaning head end 803 into his or her mouth, with the upper side (pictured) positioned with channel 801 below the teeth of his or her upper jaw. In some embodiments, which will be discussed further below, and in reference to FIGS. 9 and 10, a user may power on, activate and/or cause moving cleaning (and/or in some embodiments, treating) parts of head end 803 to begin moving and working simply by biting down, and inserting his or her teeth into channel 801. More specifically, in some embodiments, sensor(s)—such as but not limited to pressure sensors—may sense such an insertion of teeth when oral care device 800 is properly placed on the user's teeth. And, in some embodiments, such sensor(s) may sense when the teeth are completely inserted, meaning that they are inserted to a minimum required degree for cleaning and or other treatment by oral care device 801. In some embodiments, such complete insertion is sensed by sensing a sufficient length(s) of the teeth inserted. In some embodiments, such complete insertion is sensed by sensing an amount of and/or points of pressure detected in head end 803. In some embodiments, a control system 805 within oral care device 800, electrically connected or otherwise in communication with such sensor(s), may power on and/or begin actuating cleaning and/or other treatment features within head end 803, scrubbing and/or treating the user's teeth. In some embodiments, such sensor-driven actuation may take place when a mode has been activated or has not been deactivated, for example, by a bite-response mode activation button 806, electrically connected with or otherwise able to communicate with control system 805. In such embodiments, a user and/or the control system may disable bite-response mode and, in such cases, the actuation of scrubbing features in head end 803 may be initiated simply by powering on device 800—for example, by depressing power button 850. In some embodiments, a power button, or other switch or control activating a cleaning or treatment operation of oral care device 801, may instead be located on an exterior surface of oral care device 801 facing a user's tongue (e.g., near the location of drive shaft 815, discussed below), when oral care device is properly placed on the user's teeth, or at least, when oral care device 800 is at least partially inserted into the user's mouth. In some embodiments, control system 805 is a control system such as that discussed in reference to FIG. 10, below.

Prior to the placement and actuation of oral care device 800 discussed herein, a user preferably wets and fills the channel(s) of the device, such as upper channel 801, with water and a dentifrice—such as a toothpaste. To do so, a user may directly wet and fill the channels, such as channel 801. However, in some embodiments, additional, internal channel(s) and/or pump(s), within oral care device 800, release toothpaste and/or water into channels 801 when oral care device 800 is powered on and/or activated, in some embodiments. In one preferred embodiment, a filling port 807 in the housing 808 of oral care device 800 permits the filling of a storage cavity and fluid-directing channels within oral care device 800. For simplicity of presentation, that cavity and channels are not pictured, but it should be understood that they may allow the storage and flow of fluid (such as water, dentifrice and substances for treating at least part of a user's mouth) from filling port 807 to the channels 801, as well as to exit ports, such as example ports 809, of a tongue and/or mouth epithelium-scrubbing brush 811. Brush 811 may also comprise scrubbing features such as example projections or bristles 813. Brush unit 811 may be driven to rapidly move (e.g., above 20,000 hertz, in ultrasonic embodiments of the present invention), preferably in laterally shifting and/or circular motions, while generally maintaining its position, as pictured, and, thereby, oral care device 800 scrubs and cleans the user's roof of the mouth and/or tongue (in some embodiments with two channels, as discussed above, having a similar surface as shown for brush 811, facing into the page, in the perspective of the drawing). Preferably, brush 811 is comprised of a compliant material, contoured to fit the roof of a user's mouth, tongue and other aspects of the epithelium of the user's mouth. Brush unit 811 may be driven by drive shaft 815, connected to a linear actuator or other motor (not pictured) within oral care device 800 which is powered and driven by control system 805. In one embodiment, a user may cause brush 811 to be so actuated by control system 805, and/or may cause fluid to flow from, and douse, the outer surface of brush 811, by a user command—such as by a user depressing tongue brush activation button 817, which is electrically connected with or otherwise able to communicate signals with control unit 805. As with power button 850, in some embodiments, tongue brush activation button 817 may be located elsewhere, in addition to or instead of the position pictured. For example, in some embodiments, such a tongue brush activation button is located on an exterior surface of oral care device 801 facing a user's tongue, when oral care device is properly placed on the user's teeth, or at least, when oral care device 800 is at least partially inserted into the user's mouth.

Motor-driven projections or bristles, such as example bristles 819, are also preferably present within channel 801, and, in some embodiments, are attached to shafts, such as example shafts 821, each of which may be driven by a local motor in some embodiments, such as example rotary motors 822, or another, more universal cam, in some embodiments. In one embodiment, such a universal cam is a strip, connected to several bristle heads, such as any of the examples shown as 823, (or, in some embodiments, directly to the bristles), may be driven by a single, larger motor within the handle grip end 804 (not pictured).

The speed, (and, in some embodiments, the direction(s), intensity, or other aspects) of the scrubbing bristle motions discussed above may be controlled by a user-actuable speed control, in some embodiments—such as example slider 825. In some embodiments, slider 825 is also preferably electrically connected or otherwise in communication with control system 805, which, in some such embodiments, is so connected with and able to power the motor(s) driving bristles 813 and 819, as discussed above. In some embodiments, slider 825 increases the speed (and, in some embodiments, the direction(s), intensity, or other aspects) of the scrubbing bristles and other actuated cleaning or treating features when actuated in the direction toward cleaning head 803, as indicated by a speed, intensity or other aspect linear degree indicator 827.

In addition to the scrubbing motions of projections or bristles 813 and example bristles 819, and the heads, cams and other moving parts discussed above, oral care device 800 may power, drive and cause the actuation of other moving parts, cleaning and/or treating various aspects of a user's teeth and oral cavity when used as set forth in this application. Accordingly, in some embodiments, flossing features, such as example elastomeric flossers 829, are included, the motion of which may be driven in part by the same cam shafts set forth above (such as examples 821). In some embodiments, flossers 829 may be in the form of dental floss. In some embodiments, flossers 829 may each be in the form of two flexible projections, meeting one another at a leading edge when pushed between a user's teeth. In some embodiments, flossers 829 may include ports directing a line of interdental cleaning fluid between the user's teeth, as such fluid-based flossers are discussed in greater detail elsewhere in this application. In some embodiments, flossers 829 may be part of or otherwise integral with a channel-lining elastomeric layer 830, which layer hugs, conforms with and flosses the sides of teeth as it moves with the rotation (or other, e.g., shifting, movement) of motors and cams driven by control system 805, in some embodiments. As one example, pictured, when the shafts 821 shift layer 830 downward and to the left, driving bristles in the same direction, layer 830 is also pulled in that same direction. Because flossers 829 encounter the upper-right edges between two of a user's teeth, however, flossers 829 are pulled and moved against those tooth surfaces, cleaning them—which resulting conformation and position of flossers 829 are shown (without showing the teeth causing those positions, for visibility). As cams 821 rotate 180 degrees away from the position pictured, however, the other side between a user's teeth will instead be cleaned by a corresponding, opposing motion of layer 830 and flossers 829. In some embodiments, a dedicated cam shaft 831, or other drive shaft or drive line, and/or motor 833 controlled by system 805 may be used to drive each of flossers 829—in addition to motor(s) or cam(s) driving bristles 819.

Some embodiments may comprise rotary brushes, driven by rotary motors, such as example rotary brushes 835, shown lining the bottom 836 of sub-channel pocket 837, which faces the biting-surface of a tooth as it enters sub-channel pocket 837, cleaning as it is pressed against them. In some embodiments of oral care device 800, however, sub-channel pockets such as example sub-channel pocket 837, are also valves, lining an internal channel or other cavity comprising dentifrice (not pictured, but as set forth in other aspects for oral care devices discussed elsewhere in this application). In such embodiments, as a tooth enters such a pocket/valve (such as example quad-cuspid pocket 839) it unseals the valve, and allows the penetrating tooth to be cleaned and/or otherwise treated as the tooth is bathed in the fluid held in the pocket/valve. As with other valves set forth in this application, and as pictured in example pocket 839, such pockets/valves may be one-way (check valves), preventing the escape of fluid from oral care device 800 even when opened and filled with a penetrating tooth. Also as set forth in other parts of this application, spacers for allowing some amount of fluid escape, bristles or other cleaning features may be included, lining parts of tooth-interfacing surfaces of the pockets/valves, such as example quad-cuspid pocket 839.

As explained further below, control system 805 may be connected to a power source, such as a rechargeable battery and/or capacitor (not pictured) which preferably is present within oral care device 800 and grip end 804. However, in some embodiments, oral care device 800 may be externally powered (e.g., by ambient electromagnetic power).

As mentioned above, although not visible from the perspective of the figure, it should be understood that another side of cleaning head end 803, with a tooth-scrubbing channel and other features similar to those pictured for channel 801, but designed to conform to the shape of a user's teeth inset in his or her lower jaw—rather than her upper jaw, as pictured—may be included in oral care device 800, in some embodiments. Thus, in such embodiments, by biting into cleaning end 803, with a tooth entering each such pocket and/or valve of cleaning end 803, a user's full set of teeth and be completely, quickly cleaned, with very little mess.

In some embodiments, filling port 807, and the cavities and channels connected with it, and teeth-accepting channels, such as example channel 801, and brush 811, may be flushed all at once by inserting a water faucet end into filling port 807, forming a seal between them. In such embodiments, filling port 807 preferably has a ramped, elastomeric lining, enabling a seal between it and a wide variety of faucet sizes and types pressed against it for such filling.

Figure 9:
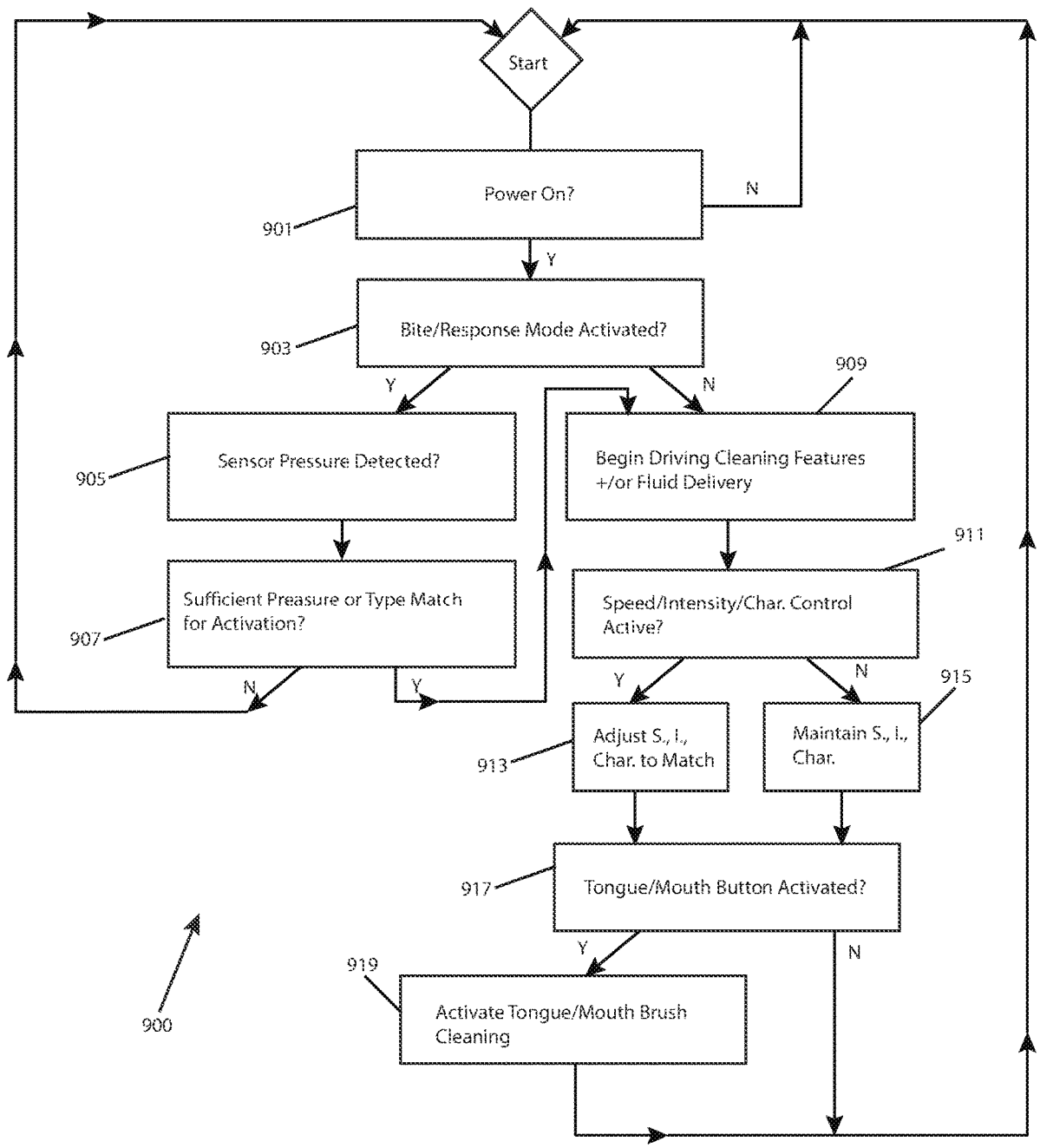
FIG. 9 is a process flow diagram depicting example steps that may taken by a control system carrying out aspects of the present invention.

FIG. 9 is a process flow diagram depicting exemplary steps that may taken by a control system carrying out aspects of the present invention, such as the control systems discussed above, and in reference to FIG. 10, below, of oral care device 800. Beginning with step 901, in some embodiments, the control system first determines whether the oral care device has been powered on, for example, by a user depressing power button 850. It should be noted that, in some embodiments, device 800 may power itself on by a switch triggered by insertion of the oral care device 800 into a user's mouth, or by inserting her or his teeth into the oral care device. In some embodiments, such a switch is a physically actuated switch, such as power button 850. In some embodiments, such a switch is actuated by passive or separately-powered sensors, e.g., detecting a sufficient amount or pattern of pressure associated with proper placement on a user's teeth and/or use of the device. Such amounts and patterns of pressure or other stimulus will be discussed in greater detail below.

If device 800 has been powered on, in some embodiments, the control system proceeds to step 903, in which it determines whether a "Bite/Response Mode" has been activated—for example, by detecting whether button 806 has been depressed. If so, in step 905, the control system may next determine whether sensors detect pressure or other activity—for example, from sensors detecting user biting pressure or teeth insertion and/or proper placement within end 803 of device 800, for example, in channel 801. If that pressure or activity is detected, the control system then proceeds to step 907, in some embodiments, wherein it determines whether the pressure (or a signal from pressure sensors) matches a recording or setting associated with proper use of device 800, for example by teeth properly seating in channel 801. For example, the control system may determine if the channels or pockets set forth above have been penetrated, and whether they are sufficiently penetrated (e.g., by detectors of whether the valves have been forced open by penetrating teeth) to indicate proper placement of the oral care device onto a user's teeth. In some embodiments, the control system compares data from the pressure sensors to pre-stored data or descriptive parameters for sensor data associated with such proper seating and, if sufficiently matching, powers and drives the cleaning features and fluid transmission aspects of end 803 discussed above, in step 909. If the Bite/Response Mode has not been activated, the control system may also begin powering and driving those features and aspects directly after step 903, in step 909.

Proceeding to step 911, in some embodiments, the control system next may take readings from a cleaning speed, intensity or other device characteristic control—such as, but not limited to, a cleaning or treatment mode of operation control, or the exemplary slider 825, discussed above—if such a control has been actuated by a user to select particular settings for the oral care device. If so, in some embodiments, the control system may proceed to step 913, in which it alters the driving power, duration, type of and amount or dentifrice or treatment fluids, or other characteristics to match the selected settings. If such a control has not been activated, in some embodiments, the control system may proceed to step 915, in which it maintains its existing power or other operative characteristics necessary to drive the cleaning features of oral care device 800 in accordance with default or previously-existing settings.

Next, in some embodiments, the control system proceeds to step 917, in which it determines whether a tongue and mouth brush, and/or other mouth epithelium cleaning and/or treatment device (such as device 811), have been activated—for example, by detecting whether button 817 has been depressed. If so, the control system begins to power and drive such a mouth epithelium cleaning and/or treatment device in step 919. The control system then returns to the starting position.

Figure 10:
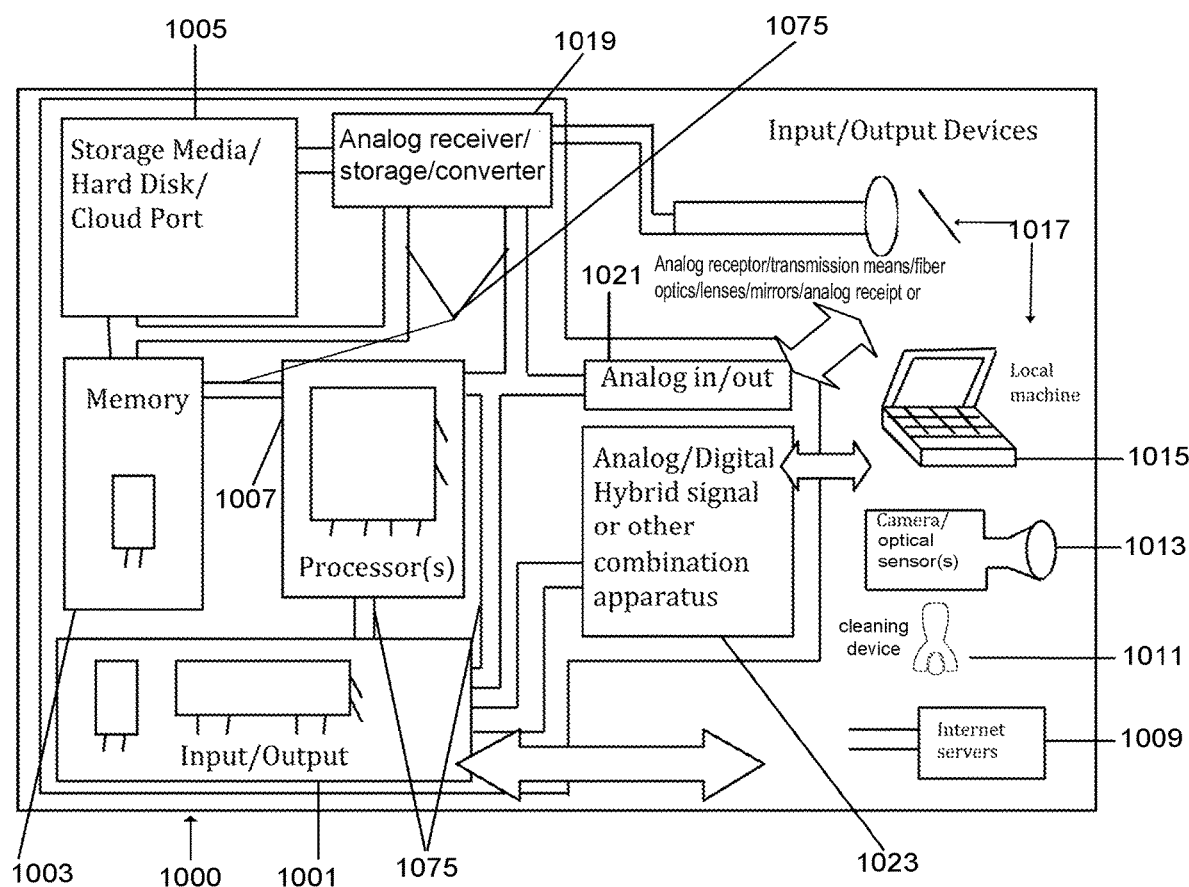
FIG. 10 is a schematic block diagram of some elements of an exemplary control system that may be used in accordance with aspects of the present invention

FIG. 10 is a schematic block diagram of some example elements of an example control system 1000 that may be used in accordance with aspects of the present invention, such as, but not limited to, operating an oral care device. The generic and other components and aspects described herein are not exhaustive of the many different systems and variations, including a number of possible hardware aspects and machine-readable media that might be used, in accordance with aspects set forth in the present application. Rather, the system 1000 is described to make clear how aspects may be implemented. Among other components, the system 1000 includes an input/output device 1001, a memory device 1003, storage media and/or hard disk recorder and/or cloud storage port or connection device 1005, and a processor or processors 1007. The processor(s) 1007 is (are) capable of receiving, interpreting, processing and manipulating signals and executing instructions for further processing and for output, pre-output or storage in and outside of the system. The processor(s) 1007 may be general or multipurpose, single- or multi-threaded, and may have a single core or several processor cores, including microprocessors. Among other things, the processor(s) 1007 is/are capable of processing signals and instructions for the input/output device 1001, analog receiver/storage/converter device 1019, and/or analog in/out device 1021, to cause a display, light-affecting apparatus and/or other user interface with active physical controls to be provided for use by a user on hardware (including, but not limited to, monitors or touch-actuable displays, and haptic feedback actuators) or other input hardware and presentation and input software (as in a GUI), and/or other physical controls.

For example, and with particular emphasis on the aspects discussed above, in connection with FIGS. 8 and 9, and FIGS. 13 and 15, the system may carry out any aspects of the present invention as necessary with associated hardware and using specialized software, including, but not limited to, GUI and other user interface aspects that may present a user with options for cleaning modes, bristle, brush and other scrubbing actuation, and speed, duration, mode and intensity controls. As another example, the system may detect pressures and characteristics from teeth sensors, controlling valves to release fluids and scrubbing features to clean teeth when sensor measurements and timing match a properly positioned and biting set of mammalian teeth engaged with the cleaning end of a device comprising said system (such as device 800). As yet another example, the system may carry out any of the steps set forth in the methods set forth in the present application.

The processor 1007 is capable of processing instructions stored in memory devices 1005 and/or 1003 (or ROM or RAM), and may communicate via system buses 1075. Input/output device 1001 is capable of input/output operations for the system, and may include any number of input and/or output hardware, such as a computer mouse, keyboard, networked or connected second computer, camera(s) or scanner(s), sensor(s), sensor/motor(s), range-finders, GPS systems, other Command and Control centers, electromagnetic actuator(s), mixing board, reel-to-reel tape recorder, external hard disk recorder, additional hardware controls and actuators, directional shading matrices, directionally-actuable light sources with variable collimation and shiftable bases, additional movie and/or sound editing system or gear, speakers, external filter, amp, preamp, equalizer, computer display screen or touch screen. It is to be understood that the input and output of the system may be in any useable form, including, but not limited to, signals, data, and commands/instructions. Such a display device or unit and other input/output devices could implement a user interface created by machine-readable means, such as software, permitting the user to carry out the user settings, commands and input discussed in this application.

1001, 1003, 1005, 1007, 1019, 1021 and 1023 are connected and able to communicate communications, transmissions and instructions via system busses 1075. Storage media and/or hard disk recorder and/or cloud storage port or connection device 1005 is capable of providing mass storage for the system, and may be a computer-readable medium, may be a connected mass storage device (e.g., flash drive or other drive connected to a U.S.B. port or Wi-Fi) may use back-end (with or without middle-ware) or cloud storage over a network (e.g., the internet) as either a memory backup for an internal mass storage device or as a primary memory storage means, or may simply be an internal mass storage device, such as a computer hard drive or optical drive.

Generally speaking, the system may be implemented as a client/server arrangement, where features of the invention are performed on a remote server, networked to the client and made a client and server by software on both the client computer and server computer. Input and output devices may deliver their input and receive output by any known means of communicating and/or transmitting communications, signals, commands and/or data input/output, including, but not limited to, the examples shown as 1017, such as 1009, 1011, 1013 and 1015 and any other devices, hardware or other input/output generating and receiving aspects. Any phenomenon that may be sensed may be managed, manipulated and distributed and may be taken or converted as input or output through any sensor or carrier known in the art. In addition, directly carried elements (for example a light stream taken by fiber optics from a view of a scene) may be directly managed, manipulated and distributed in whole or in part to enhance output, and whole ambient light information for an environmental region may be taken by a series of sensors dedicated to angles of detection, or an omnidirectional sensor or series of sensors which record direction as well as the presence of photons recorded, and may exclude the need for lenses or point sensors (or ignore or re-purpose sensors "out of focal plane" for detecting bokeh information or enhancing resolution as focal lengths and apertures are selected), only later to be analyzed and rendered into focal planes or fields of a user's choice through the system. While this example is illustrative, it is understood that any form of electromagnetism, compression wave or other sensory phenomenon may include such sensory directional and 3D locational information, which may also be made possible by multiple locations of sensing, preferably, in a similar, if not identical, time frame. Such sensors may be present, controlled by, and in communication with the control system constantly, or intermittently, and may be present within a mouthpiece of an oral care device, to aid in taking 3-D or other images, or related data, of a user's oral cavity, or parts thereof, and storing, sharing and using such images and data, as set forth in this application. The system may condition, select all or part of, alter and/or generate composites from all or part of such direct or analog image transmissions, and may combine them with other forms of image data, such as digital image files, if such direct or data encoded sources are used.

While the illustrated system example 1000 may be helpful to understand the implementation of aspects of the invention, it is understood that any form of computer system may be used to implement many aspects of the invention—for example, a simpler computer system containing just a processor (datapath and control) for executing instructions from a memory or transmission source. The aspects or features set forth may be implemented with, and in any combination of, digital electronic circuitry, hardware, software, firmware, or in analog or direct (such as light-based or analog electronic or magnetic or direct transmission, without translation and the attendant degradation, of the image medium) circuitry or associational storage and transmission, any of which may be aided with external detail or aspect enhancing media from external hardware and software, optionally, by networked connection, such as by LAN, WAN or the many connections forming the internet. The system can be embodied in a tangibly-stored computer program, as by a machine-readable medium and propagated signal, for execution by a programmable processor. The method steps of the embodiments of the present invention may be performed by such a programmable processor, executing a program of instructions, operating on input and output, and generating output. A computer program includes instructions for a computer to carry out a particular activity to bring about a particular result, and may be written in any programming language, including compiled and uncompiled, interpreted languages, assembly languages and machine language, and can be deployed in any form, including a complete program, module, component, subroutine, or other suitable routine for a computer program.

Figure 11:
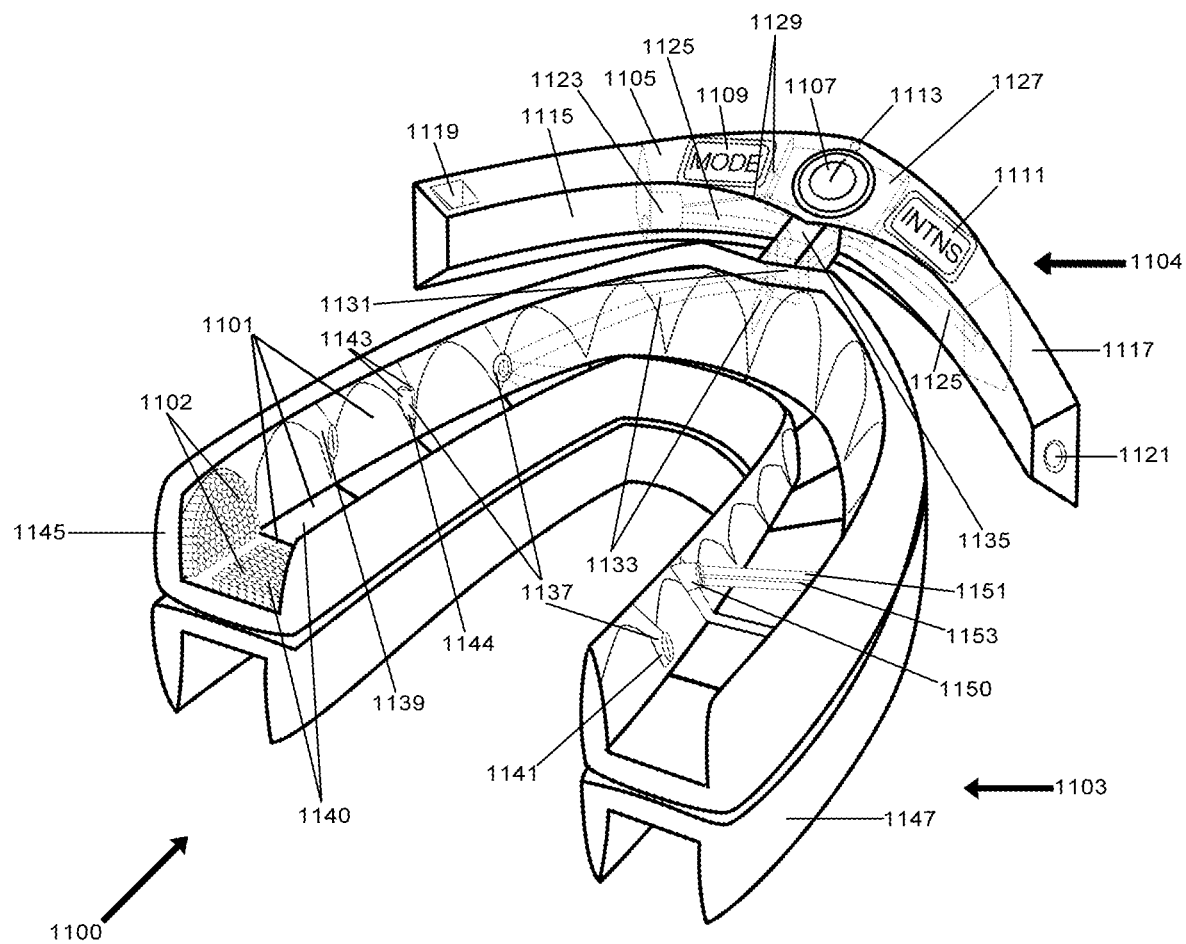
FIG. 11 is a perspective view of a new form of an example oral hygiene device, which can be used to quickly and simultaneously brush and floss each of a user's teeth and, in some embodiments, other parts of a user's mouth.

FIG. 11 is a perspective view of a new form of oral care device 1100, which can be used to quickly and simultaneously brush and floss each of a user's teeth and other parts of the user's mouth, in some embodiments. In some embodiments, which will be discussed in greater detail below, device 1100 can rapidly clean a user's entire oral cavity in under 30 seconds, with results exceeding the hygiene normally obtained with a conventional or existing electric toothbrush. Some aspects of device 1100, such as the example teeth-accepting channel 1101 and exemplary control system-actuable teeth-cleaning brushes 1102 on its surfaces (one example set of such teeth-cleaning bristles each in two example brushes being shown, only, for clarity of illustration—but it should be understood that such brushes preferably line each surface of the channel 1101, and the mirror image channel below it), are similar in nature to that shown for toothbrushes discussed elsewhere in this application. In the interests of brevity and clarity, not each of such aspects will be set forth again in full detail. However, it should be understood that any aspects of any similar oral care devices set forth in this application may be included in oral care device 1100. And several additional aspects are also set forth in this figure in this section of the application.

Figure 12:
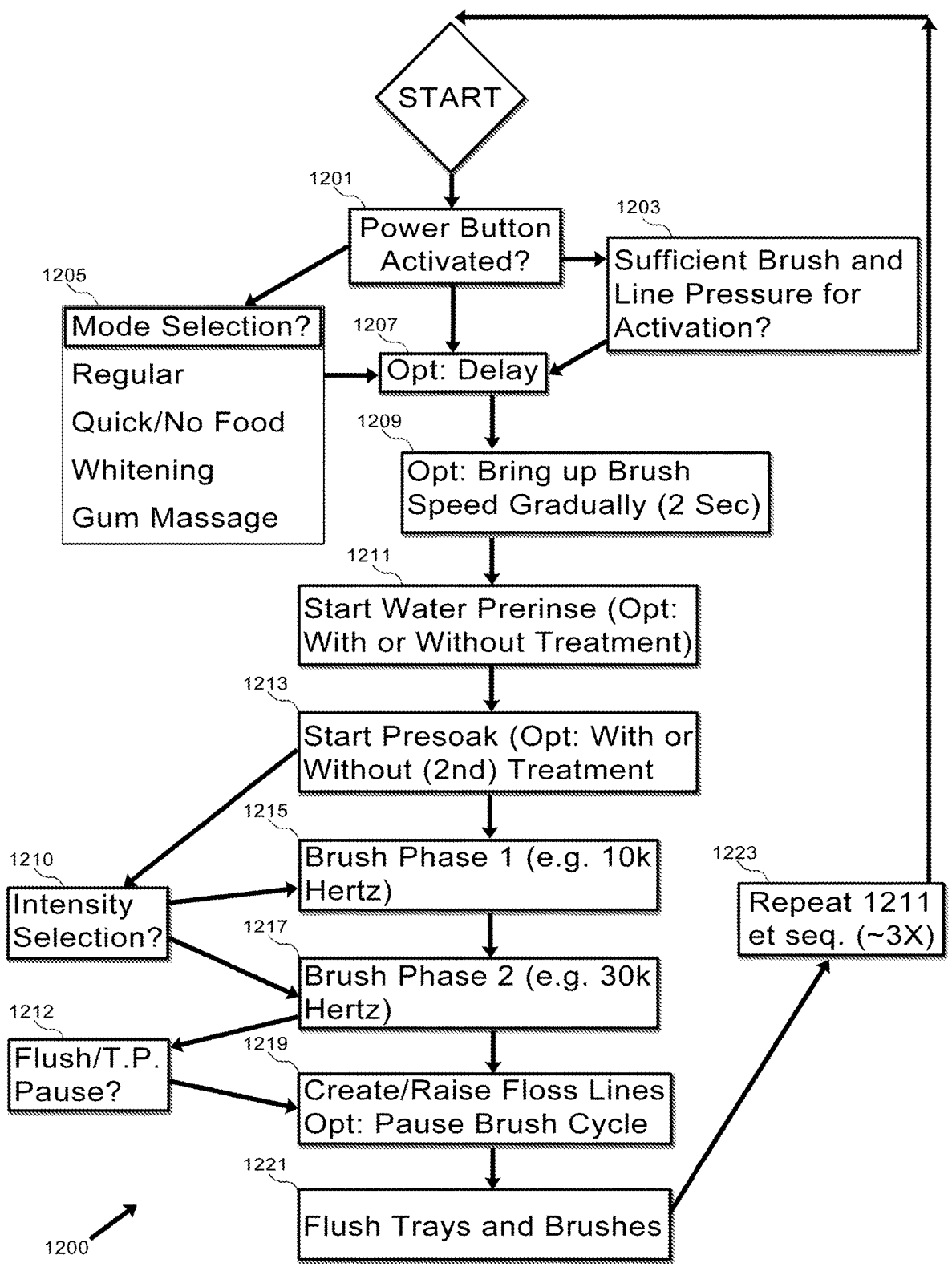
FIG. 12 is a process flow diagram depicting example steps that may taken by a control system carrying out aspects of the present invention, such as the example control systems discussed above, and in reference to FIG. 10, controlling an oral care device, such as those discussed above in reference to FIG. 11.

For example, a generally crescent-shaped handle section 1104 is now provided, as pictured. As with handle end 804 of oral care device 800 discussed above, a user can grip handle section 1104 and insert a cleaning section (in this case, U-shaped cleaning section 1103) of oral care device 1000 into his or her mouth because these two major sections are physically and, preferably, in some embodiments, rigidly attached to one another (although in other embodiments, by a flexible joint). Although unconventional, and perhaps reducing some of the leverage and ease for maneuvering device 1100 than more conventional handles, the crescent-shaped configuration of handle 1104 has many other advantages, too numerous to set forth in detail here—several of which are unique to the oral hygiene techniques set forth in the present application. Generally speaking, handle 1104 accommodates a wide range of possible horizontal handgrip positions, facilitating grip by a user's preferences, and favors the right or left hand equally. Also enhancing that grip, and the presentation and access of various user interface aspects, in some embodiments, is an upward and user-facing surface panel 1105. In various embodiments, such user interface aspects may include any and/or all of the following: a main power button 1107, a mode selection button 1109, an intensity-adjusting button 1111, and a display, such as example indicator light 1113. The function of each of such user interface aspects will be discussed herein in more detail, below, as well as in reference to the techniques set forth in reference to the next figure (FIG. 12). Also within handle section 1104, in some embodiments, are two holding tanks: A water or other solvent holding tank 1115 and a dentifrice and/or treatment substance tank 1117, which may hold a toothpaste, tooth-treating chemicals and/or other dentifrice. In some embodiments, each of these example tanks, solvent holding tank 1115 and dentifrice and/or treatment substance tank 1117, may be filled and refilled by a user, by pouring water or solvent into a valved opening 1119 to solvent holding tank 1115, or by squeezing a toothpaste or other dentifrice into valved opening 1121 to dentifrice and/or treatment substance tank 1117. In some embodiments, both of those tanks, 1115 and 1117, are preferably downward-sloped at their bases, and/or comprise pumps (such as exemplary pump 1123) to pump the fluid within them, toward and through distribution conduits—such as the examples set forth as conduits 1125. Those pumps, the user interface aspects on panel 1105 sensors, and any other active aspects of device 1100 set forth herein may be controlled and powered by a control system 1127, which may be a control system such as the control system set forth above in reference to FIG. 10, which may be electrically connected and adapted for communications with those aspects via wiring (such as exemplary wiring 1129) and/or any other means of power and communications know in the art in some embodiments. In some embodiments, the fluid contents moved through distribution conduits 1125 may be first mixed, whipped or otherwise agitated in a mixing antechamber 1131, before being further pumped (not pictured) for distribution through secondary distribution conduits, such as the examples shown as 1133 (although shown just leading to a few exemplary line-creating ports, discussed below, it should be understood that a complex of many more such conduits, leading to and separately pressurized and controlled for each and every port by the control system, or, in some embodiments, to outer- or inner-facing ports, may be included). In some embodiments, the control system 1127 may alter the mixture and amounts of each fluid component from each of the tanks (such as the example tanks 1115 and 1117), according to a mode or intensity selected by a user (using mode selection button 1109 or intensity selection button 1111 or, in some embodiments, data from sensors—for example, by metering out different amounts of fluid from each of tanks 1115 and 1117 through controlled valves or pumps conducting fluid from the tanks to mixing antechamber 1131. In any event, the mixed fluids (which may, in some embodiments, be, alternatively, isolated in separate distribution conduits, and released in controlled amounts at the point of use, a user's teeth) are next conducted to cleaning section 1103, across a bridge 1135 adjoining that section with handle section 1104, via secondary distribution conduits 1133.

Upon entering cleaning section 1103, in some embodiments, the mixed fluids are sent to numerous ejection ports, such as example ports 1137 which each create at least one flossing line (a.k.a., projections, or jets) via the resulting ejection of a stream of fluids. Although the example of flossing line establishing ports 1137 are given, it should be understood that a wide variety of other forms of ports, slides, diffusion matrices or transmission materials, siphons or other transmission techniques may, alternatively or in addition, be used to transmit the fluids into contact with the user's teeth, gums, between interdental spaces, about the user's teeth, and the remainder of his or her oral cavity, in various alternative embodiments. In the embodiments shown, the ejection of fluids through each of ports 1137 is preferably forcibly pulsed according to a timing and pattern of force set forth in the particular use mode selected by a user (and carried out by control system 1127). Also preferably, there are at least two ports, situated at a point of division between two tooth-cradling pockets (such as exemplary pockets 1140), and dedicated to establishing flossing lines between each gap in a pair of user's teeth. One of those ports, such as example port 1139, is located at the outward-facing surface of the user's teeth, while the other, such as example port 1141, is located at the inward-facing surface of the user's teeth, when a user has placed section 1103 within his or her mouth, and inserted each of her teeth into pockets 1140. Preferably, in most usage modes, only one of each of those two opposing pairs of ports at each gap is active, ejecting the fluid, at a given time, and the force with which it is expelled is sufficient to fully penetrate and clean the gap between the user's teeth to which the pair of ports is dedicated, as well as the gap between the teeth and gums. To prevent fluid from the active port entering the opposing, inactive port, port-tightening water-foils 1143 may be included about the outer surface of each port—as shown in exemplary port 1144—in some embodiments. In some embodiments, such as that pictured with exemplary port, the material comprising the flossing lines that they create may be more rigid than with the use of an ejected fluid. In the example pictured with port 1150, for instance, a flattened flossing tape 1151 is gripped by a pair of opposing ports (of which port 1150 is one). In some embodiments, such flossing tape 1151 may have central ridges 1153 with edges to aid in brushing between the user's teeth. This is especially effective in embodiments, such as that pictured for port 1150, where the control system can raise, lower and vibrate the flossing line (with motors attached to each of the ports, and an open channel for port 1150 to travel within) between the user's teeth, and even under the gums by actuating the angle of the tape (e.g., with a rotary motor or gimble changing the angle of the leading edge of the floss line). Similarly, with fluid floss lines the flossing fluid ejected from the ports may have a wide variety of differing angles of ejection, including directions entering under the gum line, in various embodiments. For example in some embodiments, the angle of ejection of the ports differs depending on the exact fluid pressure applied by the control system. A resting conformation of the port that points more upward, for example, results in a higher angle of ejection, into the user's gums, when a lower pressure of ejection is caused by a variable-pressure pump controlled by the control system. But if a higher pressure is applied, and the elastomeric components of the port are stretched more greatly, the resulting extending conformation results in a more lateral angle of pressure for the resulting flossing line. Of course, any of the above flossing devices may be used in channels accommodating any number of a user's teeth, rather than the exact number pictured—that example being exemplary only.

As with oral care device 800, oral care device 1100 may also comprise a motorized tongue brush, or other oral cavity brush attached to and powered by the device and conforming to any surface of the user's oral cavity or throat, and also controlled by control system 1127. Also as with oral care device 800, and more visible in the present figure, 2 sets of tooth-accepting channels are present namely, an upper set of tooth-accepting and -cleaning channels 1145 and a lower set of tooth-accepting and -cleaning channels 1147. Each set 1145 and 1147 is generally U-shaped to match and conform with the contour of a user's two rows of teeth (in the instance of a human user) in some embodiments. In some embodiments, the sets are custom-molded to the exact impression or 3-dimensional shape of each user's mouth, for example, by comprising a heat-conformable material to match a mold of the user's teeth. An inner material, on which other structural components, may be of greater rigidity and less susceptible to such a molding process, or, in some embodiments, separated from the remainder of device 1100 during custom-molding (or vice versa, with a conformable outer shell separable from the remainder of the device during molding). Other adjustments, such as brush sizes and extensions, and the addition and exact positioning of ports, may also be custom-fit onto the device in some embodiments, after or as part of the molding process, avoiding the dangers of heat or other chemicals facilitating molding by adding those other components to the molded components later.

Although the example of dentifrice, water and other fluid-containing tanks has been provided, it should be understood that any suitable form of storage and conduit may, alternatively or in addition be used, in some embodiments. In some embodiments, only one tank, for dentifrice toothpaste or other mouth washes, may be included, while water is simply applied to device 1100 and/or its brushes. In still other embodiments, external storage tanks, connected to device via flexible conduits, may instead be used. As yet another alternative embodiment, cartridges (not pictured in the present figure) holding the fluid(s), may be inserted into device and exchanged out when depleted, rather than having a permanent, on board storage tank(s).

Also, although the example of bristled brushes, similar to a conventional toothbrush, has been provided, it should be understood that any form of brush suitable for cleaning tooth surfaces may be used for any tooth-cleaning device set forth herein, in various embodiments. In some embodiments, a rubberized, non-porous material, with cleaning ridges may be used. In other embodiments, ultrasound or other waves or vibrations may be used for cleaning, rather than brushes. For example, even the fluid ejected from the flossing ports may include a vibrational actuator, and/or ultrasound for moving the fluid, surrounding air or other fluid ejected from the ports or surrounding the user's teeth. Preferably, a combination of more than one of each of these approaches is included, and cycled in a mode for optimally, or deep-cleaning the user's teeth.

FIG. 12 is a process flow diagram depicting exemplary steps 1200 that may taken by a control system carrying out aspects of the present invention, such as the control systems discussed above, and in reference to FIG. 10, controlling bite-actuable oral care device 1100.

Beginning with step 1201, in some embodiments, the control system, such as the control system set forth above in reference to FIGS. 10 and 11, first determines whether oral care device 1100 is powered on (e.g., by a user depressing main power button 1107), meaning that the control system is receiving power from a power source (e.g., a local lithium-ion battery with sufficient power to power the operations of the control system and device 1100.) If not, in some embodiments, the control system may indicate that recharging is necessary (for example, by causing its display 1113 to flash yellow). In some embodiments, the control system may next proceed to step 1203, in which it further determines whether a user has inserted his or her teeth sufficiently into the teeth-accepting channels of device 1100 before proceeding (e.g., with pressure sensors, and requiring a sufficient number and pressure within the teeth-accepting channels of the device). Next, in step 1205, the system next determines what mode the user has selected for use of the device, in some embodiments. For example, in a regular mode, a regular or default length of time, intensity or length of brush strokes, type of brush movement or ultrasound or other vibration levels or characteristics may be selected and carried out by the control system when actuating ports, brushes and other aspects of the device. In other, more brief modes, a user may indicate that a faster clean (e.g., when no food has been consumed, in the morning) is desired, and the system will carry out a less vigorous, less lengthy, cleansing routine, in some embodiments. In a more intense than default mode, by contrast, such as a whitening mode, the system may carry out a more vigorous, deep-cleaning and lengthy routine, in some embodiments, when carrying out the remainder of the steps set forth in this figure. As yet another example, a mode emphasizing the cleansing and massaging of the gums—for example, with the lower pressure ejection actuation discussed above—may be carried out.

However, if power has been activated and is sufficient, and regardless of the mode selected, the control system then proceeds to step 1207, in some embodiments, in which it first implements a delay while readying the cleansing routine. Proceeding to step 1209, in some embodiments, the control system may begin to power the brushes and flossing lines of the device, but in a graduated, slowly accelerating manner. In step 1211, and as speed is slowly building, in some embodiments, the system may pump water through the ejection ports, with an increasing amount of dentifrice, pre-rinsing the user's teeth. In some embodiments, the device also flushes water and debris in this step, potentially activating a valve to release fluid, draining it away from the device and into a storage container within the device (or into the user's sink through a release hatch). Proceeding to step 1213, the system may begin to increase the amount of dentifrice and treatment fluids, soaking the user's teeth, in some embodiments. In steps 1215 and 1217, in some embodiments, the system may begin to increase the cleansing activity and speed of the brushes, in stages. In step 1219, in some embodiments, the system may begin to actuate the floss lines of the device and, in some embodiments, threading them into the user's teeth, while, in others, creating lines of fluid, as set forth in greater detail above. At any point during this routine, the system and/or the user may elect to flush the device with water, and/or pause the scrubbing activity of the flossing and brushes, in optional steps 1210 and 1212 and 1221. Finally, the control system may repeat any of these steps, before returning to the starting position, in step 1223.

Of course, in some embodiments, the tooth brushing aspects of the invention set forth in this application may be provided in oral care device 1100 without the flossing-related aspects, and only the tooth-brushing related steps set forth above may be carried out, without the steps related to flossing, in some such embodiments. Conversely, in other embodiments, the flossing-related aspects of the invention set forth in this application may be provided in oral care device 1100 without the tooth-brushing related aspects, and only the flossing-related steps set forth above may be carried out, without the steps related to toothbrushing, in some such embodiments.

Figure 13:
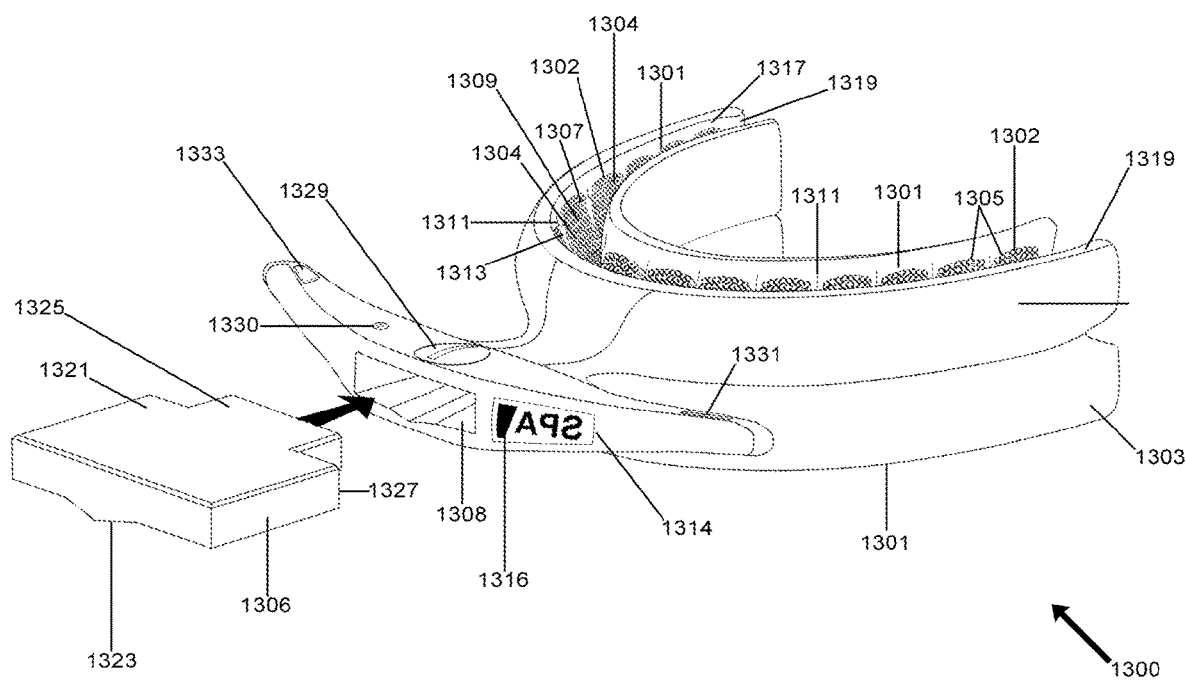
FIG. 13 is a perspective view of another example oral care device with a generally U-shaped mouthpiece, along with an example cartridge and cartridge loading compartment shaped according to a complementary proprietary form factor, and other unique embodiments of the present invention.

FIG. 13 is a perspective view of another example oral care device 1300 with a generally curved (in the example pictured, U-shaped) mouthpiece 1303, along with an example cartridge 1306 and cartridge-loading compartment 1308, shaped according to a proprietary form factor complementary to the human form, and other unique embodiments of the present invention. As with the oral care device set forth above, in reference to FIG. 11, in some embodiments, oral care device 1300's mouthpiece, such as the example U-shaped mouthpiece 1303, includes teeth-accepting channel(s), such as teeth-accepting channel(s) 1301 for accepting each of an upper and lower set of a user's teeth. In the example pictured two such channels, an upper and a lower channel, are provided, for accepting respectively, a user's upper and lower sets of teeth. Also as with other oral care devices set forth in the present application, in some embodiments the teeth-accepting channel(s) 1301 include several example control system-actuable teeth-cleaning brushes, such as the example teeth-cleaning brushes 1302 pictured, each of which may be powered and controlled by a control system at least partially within oral care device 1300. In some embodiments teeth-cleaning brushes may have a different shape than some of the specific examples of teeth-cleaning brushes provided elsewhere, however. For example, in some such embodiments, teeth-cleaning brushes 1302 are provided with curved surfaces, such as the examples shown as curved surfaces 1304, formed by the heads of the bristles, such as example bristles 1305, of each of the teeth-cleaning brushes, such as the example teeth-cleaning brushes 1302. In some embodiments, those curved surfaces, such as the example shown as example curved surfaces 1304 are curved to conform to and match the outer surface curves of a user's teeth and gums. In some such embodiments, curved surfaces 1304 include an upward-pointing ridge 1307, angled toward, and matching, the gum-line of a user of oral care device 1300. In some embodiments, curved surfaces 1304 form a plurality of concave, tooth-hugging pockets, such as the example shown as 1309, into which a user may insert each of his or her teeth. In some such embodiments, interdental inserting ridges, such as the examples shown as 1311, are disposed between each of tooth-hugging pockets 1309, which may aid in cleaning between the user's teeth. In some embodiments, liquid-releasing jets, such as the example pictured as liquid-releasing jet 1313, are included, and also disposed between each of tooth-hugging pockets 1309. Such liquid-releasing jets may also aid in cleaning between a user's teeth, in some embodiments. In some embodiments, the liquid-releasing jets also introduce fluids including materials for treatments other than cleansing. For example, in some such embodiments, such materials include tooth whiteners, such as bleaching or deep-cleaning treatment materials. In some embodiments, such materials include gum-massaging and moisturizing materials. In some embodiments, such materials include anti-oxidants. In some embodiments, such materials include fluoride. In some embodiments, such materials include a breath freshener. In some embodiments, such materials include an anti-microbial material, such as an antibiotic. In some embodiments, such materials include a pre-biotic or pro-biotic material. In some embodiments, such materials include a vitamin. In some embodiments such materials include a mineral. In some embodiments, such materials include alcohol.

In some embodiments, liquid emptying ports (not pictured) are also provided within teeth-accepting channels 1301, which may be connected to, and empty fluids from teeth-accepting channels 1301. In some embodiments, such emptied fluids may be pumped or otherwise fed through disposal channels (not pictured) within U-Shaped mouthpiece 1303, to a disposal tank (not pictured). In some such embodiments, such disposal channels and/or a disposal tank are at least partially within a handle of oral care device 1300, which may be a U-shaped, V-shaped, C-shaped or hyperbolic-shaped or parabolic-shaped, or other curved handle—such as example U-shaped handle. (In some embodiments, handle may be, or may partially be, linear or otherwise straight-edged, however.) In some embodiments, jets 1313 are fed by fluid-directing channels. In some such embodiments, those fluid-directing channels may cycle some of the same fluids and materials as the disposal channels. In some such embodiments, some such fluid-directing channels and disposal channels may be the same channels. For example, in some such embodiments, materials and fluids may be cycled through jets 1313 into the teeth-accepting channels 1301, where they may be agitated and applied to a user's teeth, gums and oral cavity with the aid of motorized brushes, such as teeth-cleaning brushes 1302, and then removed from the teeth-accepting channels 1301 by such liquid-emptying ports, and then back out through jets 1313, and so on. In some such embodiments, such a process continues for a duration set by a user and/or the control system of oral care device 1300. In some such embodiments, such a process continues at particular rate(s) or intensity level(s) (e.g., pressure of liquids emitted from jets 1313) or patterns thereof. In some such embodiments, such rate(s), intensity level(s) or patterns thereof are defined by a mode of operation, which can be set from a number of options, by a user and/or a control system controlling oral care device 1300. Some of those modes and related methods are discussed in greater detail below, in reference to FIG. 14. In some such embodiments, such a mode is indicated to a user via a mode indicator. For example, in the example pictured, a display 1314 indicates to a user that oral care device 1300 is currently being, or was most recently, operated in a "Spa" mode, by displaying the word "SPA". In some such embodiments, such a display displays a mode indicator, along with other data to a user, such as time or duration indicator 1316. In some embodiments, such a time or duration indicator indicates to a user how much time has elapsed and/or is remaining in a cleaning or treatment regimen. In some embodiments, display 1314 displays such indicators in a backwards readout, such that, when a user looks in the mirror with oral care device 1300 inserted in his or her mouth, he or she sees a non-reversed image of any words displayed by display 1314.

In some method embodiments of aspects of the present invention, a 3-D image of at least part of a user's mouth is taken, and the shape of the curved surfaces formed by the brush head bristles, such as example curved surfaces 1304, is created to conform to and match that part of a user's mouth. For example, in some embodiments, a dental mold may be taken of the inside of a user's mouth, and the shape (including size) of the curved surfaces are created with a shape conforming to the shape and dimensions of the dental mold. In some embodiments, a 3-D scan may be taken of the inside of a user's mouth, and the shape (including size) of the curved surfaces are created with a shape conforming to the shape and dimensions of the 3-D scan. In some embodiments, such a 3-D image may be taken of a user's teeth, teeth and gums and/or oral cavity.

In some embodiments, the specific shape of U-shaped mouthpiece 1303 may also, or alternatively, be created to conform to and match a part of a user's mouth. In some such embodiments, a 3-D image of at least part of a user's mouth is taken, and the shape of the outer surface 1315 of U-shaped mouthpiece 1303 is created to conform to and match that part of a user's mouth. In some embodiments, a dental mold may be taken of the inside of a user's mouth, and the shape (including size) of the outer surface 1315 of U-shaped mouthpiece 1303 is created with a shape conforming to the shape and dimensions of the dental mold. In some embodiments, a 3-D scan may be taken of the inside of a user's mouth, and the shape (including size) of the outer surface 1315 of U-shaped mouthpiece 1303 is created with a shape conforming to the shape and dimensions of the 3-D scan.

In some embodiments, the curved surfaces formed by the brush head bristles, such as example curved surfaces 1304, may be integrated with one another, forming a single brushing surface, capable of contacting, brushing and/or treating all of a user's teeth simultaneously. In some such embodiments, such curved surfaces may also contact other parts of a user's mouth such as the gum-line, simultaneously with so contacting all of a user's teeth. In some embodiments, each of the teeth-cleaning brushes, such as the example teeth-cleaning brushes 1302, is actuated by a separate motor, controlled by a control system of oral care device 1300. In some such embodiments, a removable liner 1317 may include a plurality of removable brackets (not pictured), each of which is reversibly connected to one of such motors. In some such embodiments, the size and contours of removable liner 1317 may be created based on any of the 3-D imaging or information techniques for creating the curved surfaces formed by the brush head bristles, or for creating the outer surface 1315 of U-shaped mouthpiece 1303, as discussed above. In some embodiments, removable liner 1317 may be waterproof. In some embodiments, removable liner 1317 may be permanently attached to, or otherwise integrated with, the remainder of oral device 1300. In some embodiments, water or fluid-tight seals, such as example rubber seal 1319, may be included in U-shaped mouthpiece 1303, and configured to, with the user's gums against which they press while installed in a user's mouth, form a liquid- or other fluid-tight barrier, preventing the escape of liquid or other fluids from teeth-accepting channel(s) 1301 while using oral care device 1300.

As mentioned above, in some embodiments, oral care devices in accordance with aspects of the present invention may hold and distribute water, dentifrice, treatments, and other oral care materials from standardized packages, which may be temporarily, reversibly connected to fluid conduits of the oral care devices, to at least part of a user's oral cavity, such as her or his teeth, gums, tongue, sublingual areas, the roof of the mouth, and throat. In some embodiments, such standardized packages may be issued and delivered from a remote source, which may be controlled, at least in part, by a control system and/or a medical authority, such as a dentist. For example, and also as mentioned above, in some embodiments, specialized, standardized cartridges, such as example cartridge 1306, may be so issued. In some embodiments, such standardized packages (e.g., cartridge 1306) may include one or more part(s) with a proprietary format, to ensure that only correct cartridges, approved for use with the particular type of oral care device, are installed onto or into the oral care device. For example, cartridge 1306 is pictured with an unusually-shaped housing 1321, shaped according to a proprietary, unusual form factor—namely, in this example, an elongated, V-shape of particular proportions, angles and dimensions. As a result, a lower surface 1323 conforms with that proprietary, unusual form factor. Similarly, a cartridge-loading compartment 1308 is also shaped according to the same, proprietary, unusual form factor, albeit in reverse (bas-relief) to the shape of cartridge 1306, such that cartridge-loading compartment 1308 and cartridge 1306 have a complementary, inverse 3-D form factor relative to one another. As such, and as pictured, cartridge 1306 may be installed into compartment 1308 by sliding end 1325 of cartridge 1306 into cartridge-loading compartment 1308, as pictured by force/motion vector arrow 1326. In some embodiments, the proper degree of insertion for such installation is ensured by stops 1327, which arrest further insertion at the correct length to ensure the seating of internal connectors (not pictured) between cartridge 1306 and cartridge-loading compartment 1308. As mentioned above, some of such connectors may be conduits from an internal tank holding such oral care fluids within cartridge 1306, and conduits within oral care device 1300 which deliver fluids to a user's oral cavity. For example, in some embodiments, such conduits within oral care device 1300 connect with ports 1313, delivering fluids from cartridge 1306 to teeth-accepting channel(s) 1301. In some embodiments, such conduits within oral care device 1300 and such conduits from an internal tank of cartridge 1306 may comprise connecting ports, with a complementary form factor for physically interfacing with one another. In some embodiments, such ports include valves which are forced open upon such physical interfacing. In some embodiments, such valves electrical actuators, which are controlled by a control system, which may be present within cartridge 1306 and/or oral care device 1300. For example, in some such embodiments, such a control system may be a control system such as that disclosed in reference to FIG. 10. In some embodiments, multiple such internal tanks may be present in cartridge 1306. In some embodiments, such an internal tank may be present within oral care device 1300. In some such embodiments, such an internal tank may be present within oral care device 1300 and may receive cleaning and treatment fluids from cartridge 1306, which may then be decoupled from oral care device 1300 prior to use.

Of course, such a control system within oral care device 1300 may carry out a number of methods and steps aside from controlling the channeling and release of cleaning and treatment oral care fluids. For example, with or without user input, such a control system may carry out steps of any of the methods set forth in the present application. Some such example steps are set forth below, in reference to FIG. 14.

Such user input may be created and received via user controls, in some embodiments. For example, in some embodiments, a power button and/or switch 1329 may be provided. In some such embodiments, a user pressing power button and/or switch 1329 causes oral care device 1300 to power up, delivering power from an internal or external power source to part of the control system. In some such embodiments, a lighted indicator display 1330 may be used to indicate whether device 1300 has been so powered up. For example, in some embodiments, such a power source may be a battery (not pictured) within oral care device 1300. In some embodiments, such a power source may be an external, wireless power source, and oral care device may include a wireless power receiver. In some embodiments, a wired power source may be connected to device 1300 (e.g., by a power cable from a wall outlet or external power pack.) As mentioned above, oral care devices may include a number of operating modes and durations of operation, which may be selected by such a control system, or a user, by entering input through such user controls. For example, in some embodiments, a user may select or request a mode of operation of oral care device 1300 with a mode selection button 1331. In some embodiments, other aspects of device 1300's performance may be selected using a performance option selection button 1333. In some such embodiments, such a performance option may be a duration of operation. In some such embodiments, such a performance option may be an intensity level of operation. In some such embodiments, such an intensity level of operation may be a fluid pressure level. In some embodiments, such an intensity level of operation may be a speed of brush movement. In some embodiments, such an intensity level may relate to an amplitude of ultrasound generated by device 1300. For example, in some modes of operation, oral care device 1300 may include ultrasound emitters. In some such embodiments, such ultrasound emitters target a user's teeth. In some embodiments, such ultrasound emitters target brushes of oral care device 1300. In some embodiments, such ultrasound emitters target fluids emitted by oral care device 1300. As also mentioned above, such modes may be affected by parameters or other rules set forth by a control system and/or a central authority, for optimizing the oral care of a user. In some embodiments, such modes and durations of use may be indicated to a user via feedback. For example, in some embodiments, such feedback is haptic feedback, delivered by a haptic actuator within oral care device 1300. In some embodiments, such feedback may be visual, delivered via a display (such as example display 1314), as explained above. In some embodiments, observations may be made by such a control system, or user operating such a control system, within oral care device 1300 and/or 1306, or a control system variably connected with such control system(s). In some such embodiments, sensors are located within mouthpiece 1303, and connected with such a control system. In some embodiments, such sensors may be a camera. In some embodiments, such sensors may detect changes in the condition of a user's mouth, at different times, as will be discussed in greater detail below. For example, in some such embodiments, such sensors may detect plaque and/or tooth decay. In some embodiments, such sensors may detect gum bleeding. In some embodiments, such sensors may detect a soil level of a user's teeth and/or mouth. In some such embodiments, such sensors are coupled with a light source, such as a flash. As will be discussed further below, some such detection is carried out by comparing images obtained through such sensors of parts of a user's oral cavity over time and/or two standard images and data related to various oral health related conditions. In some such embodiments, a library of such standard images in data, for such comparisons (e.g., by confidence interval matching).

Figure 14:
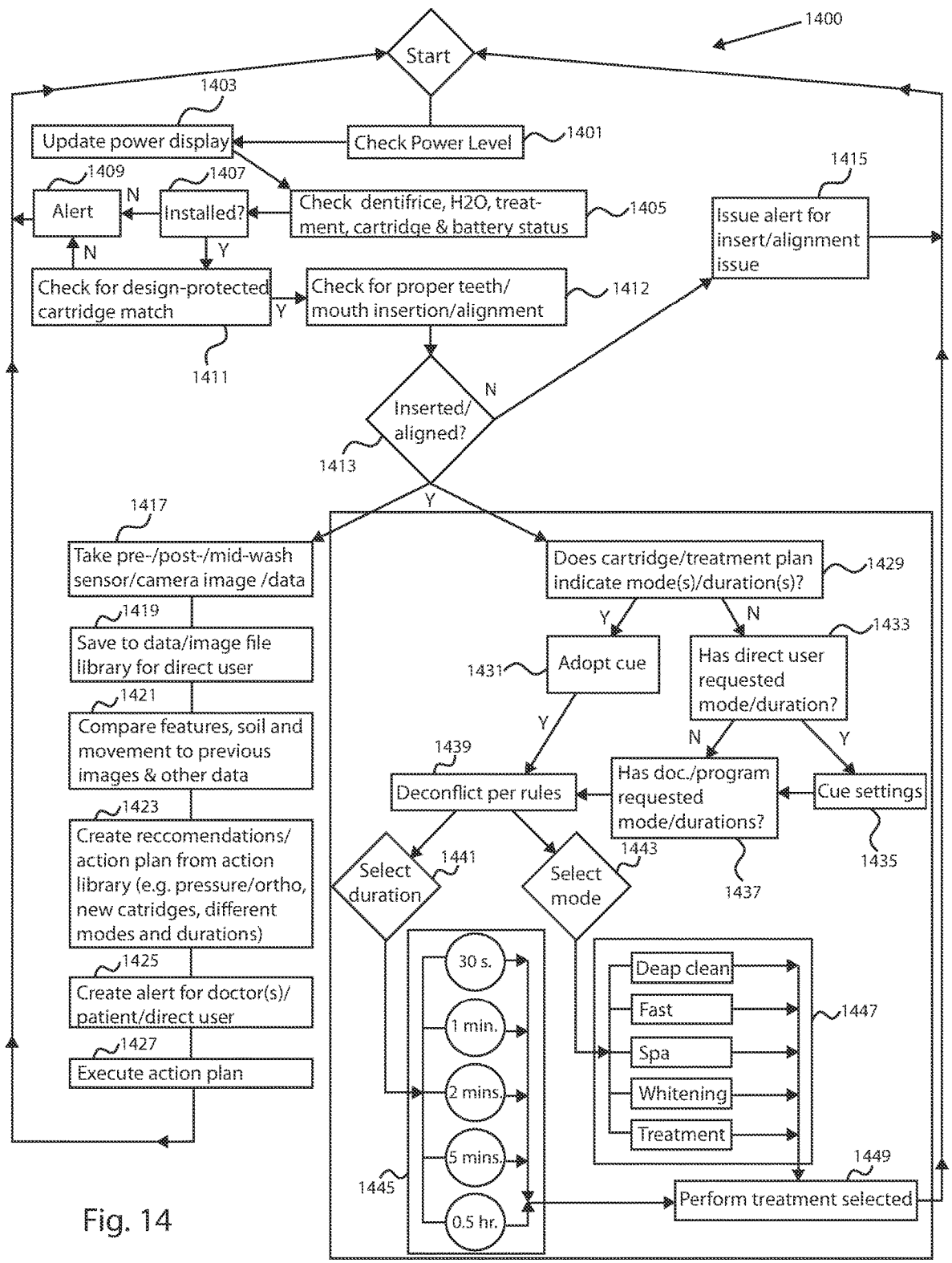
FIG. 14 is a process flow diagram depicting example steps that may taken by a control system carrying out aspects of the present invention, such as the example control systems discussed above, and in reference to FIG. 10, controlling an oral care device, such as those discussed above in reference to FIG. 13.

FIG. 14 is a process flow diagram depicting example steps 1400 that may taken by a control system carrying out aspects of the present invention, such as the example control systems discussed above, and in reference to FIGS. 10 and/or 11, controlling an oral care device, such as those discussed above in reference to FIG. 13.

Beginning with step 1401, the control system, such as the control system may first determine whether the oral care device (such as oral care device 1300) is powered on (e.g., by a user actuating power button and/or switch 1329), meaning that the control system is receiving power from a power source (e.g., a local lithium-ion battery with sufficient power to power the operations of the control system and device 1300) and may assess the power level available for use by the oral care device. In some embodiments, the control system may indicate that power level to the user in step 1403 (for example, by causing its light display 1330 to flash red to signify low power, or by a graphic display, such as example display 1314 to provide a readout indicating a power state to a user, and/or by providing haptic feedback). In some embodiments, the control system next proceeds to step 1405, in which it assesses (e.g., via sensors within fluid-containing tanks of oral care device 1300, or cartridge 1306) a fluid/fill level for each type of fluid present in each fluid-containing tank of oral care device 1300 and/or cartridge 1306. For example, in some embodiments, the control system assesses a water tank level. In some embodiments, the control system assesses a dentifrice level. In some embodiments, the control system assesses another level for another treatment material. In some embodiments, the control system also assesses a battery state, for a control system within oral care device 1300 or cartridge 1306. In some embodiments, the control system may fail to read, or fail adequately to read, such a level within cartridge 1306, for example, due to a connection error due to improperly aligned or insufficiently inserted electrical contacts between cartridge 1306 and oral care device 1300, and determine that the cartridge, or fluids within it, have been incompletely, or incorrectly installed, in step 1407. In some such embodiments, an alert may be issued to the user, in subsequent step 1409 (through any display, haptic feedback device, or other suitable communications mechanism, in some embodiments). Similarly, if, in step 1411, the control system determines that a non-proprietary, or unauthorized cartridge has been installed in device 1300, it may also issue such an alert to a user. In some such embodiments, such a determination may be made by a failed authentication challenge between the control system and an authentication device within the cartridge.

In some embodiments, the control system may next proceed to steps 1412 and 1413, in which it further determines (e.g., via sensors) whether a user has properly inserted a mouthpiece of the oral care device into her or his mouth, or has inserted his or her teeth sufficiently into the teeth-accepting channels of the oral care device (e.g., 1300) (e.g., with pressure sensors, and requiring a sufficient number and pressure within the teeth-accepting channels of the device) before proceeding. If the control system determines that the user has not properly inserted a mouthpiece of the oral care device into her or his mouth, or has not inserted his or her teeth sufficiently into the teeth-accepting channels of the oral care device, the control system may proceed to step 1415, in some embodiments, in which it issues an alert that there is an installation or device alignment issue to the user, via any of the communications methods set forth in this application, and then returns to the starting position. Assuming that the user has properly inserted a mouthpiece of the oral care device into her or his mouth, and has inserted his or her teeth sufficiently into the teeth-accepting channels of the oral care device, the control system may simultaneously proceed to steps 1417 et seq. and, in some embodiments, in parallel, to steps 1429 et seq.

Proceeding to step 1417, the control system may first take images (e.g., from a camera within oral device 1300, such as example camera 1351, or other sensor readings from other sensors detecting aspects of the inside of a user's mouth, and stores data related to those images or other readings within a library of such data related to the user in step 1419. For example, in some embodiments, the control system may store images or other readings of a user's teeth and/or gums. In some embodiments, the control system may store images or other readings of a user's tongue. In some embodiments, the control system may store images or other readings of a user's mucous membrane. In some embodiments, the control system may store images or other readings of a user's roof of the mouth. In some embodiments, the control system may store images or other readings of a user's throat. In some embodiments, the control system may store images or other readings of a users' sublingual area. In some embodiments, the control system may store images or other readings of a user's breath. In some embodiments, the control system may store images or other readings of other aspects of a user's mouth. In some embodiments, the control system may take particular readings and data as ordered by, and relay those readings and data to, a third party authority, such as the user's dentist. The control system may then proceed to step 1421, wherein it compares those images and other readings, or data based on them, to previously-stored data and readings, or data related to other images and readings stored by the control system. In some such embodiments, the other images and readings stored by the control system may be previously stored images and readings for that user, and the control system may generate a comparison between the data related to the most recent images and readings and the previously stored data related to images and readings for that user. In some embodiments, the control system may compare data related to the most recent images and other data stored by the control system. For example, in some such embodiments, such data relates to conditions or changes in conditions within a user's mouth indicating a particular disease, ailment or disorder. In some such embodiments, images or readings of particular features of a user's mouth may be compared to features associated with such conditions, such as plaques or cavities. As another example, in some such embodiments, such data relates to conditions or changes in conditions within a user's mouth indicating a positive health condition for human's oral hygiene and health. Based on such data and comparisons, the control system may next generate recommendations for the user, and an action plan for the performance of cleaning and other treatments by the oral care device (or otherwise, such as by a dentist), from a library of such action plans for redressing any conditions associated with, or otherwise indicated, by those data and comparisons, in step 1423. For example, in some embodiments, such an action plan may be a prescription of actions and certain fluids or other treatments to be administered to a user's teeth and/or mouth via the oral care device, in particular modes of operation and durations of use of oral care device 1300. In some such embodiments, cartridges containing such treatments, and/or commanding such actions (e.g., with coding within a data storage device within the cartridge) may be issued to the user by a central authority, in communication with, or included within, the control system. In some embodiments, a dentist or other oral care provider may alerted to the conditions so identified, the action plan prescribed and/or other the recommendations and information obtained and created by the control system, in step 1425. The user, using the oral care device 1300, may then begin to carry out that action plan, in step 1427.

Such an action plan preferably includes a number of steps carried out (e.g., periodically) with the oral care device. Thus, as mentioned above, when the control system proceeds to step 1429, in some embodiments, the control system may assess whether a treatment plan or action plan based on a treatment plan and/or an inserted cartridge within the oral care device contains instructions, cuing up and indicating which actions are to be undertaken by the oral care device for a particular user. If so, the control system may proceed to step 1431, in which it adopts such cues, and readies the actions indicated. For example, in some embodiments, readings and data may have indicated that a user is developing plaque, or yellowing teeth. Accordingly, in such an embodiment, an treatment plan including actions to address that plaque and reverse it, may be cued, and the oral care device may be readied to carry out such actions (e.g., more vigorous brush actions, for a greater duration, with an anti-gingivitis dentifrice, and anti-microbial treatments). Other sources of requested actions by oral care device 1300 may, of course, also be made. For example, in some embodiments, the control system may determine whether it has received requests from the user to carry out particular modes of use, durations and other operation parameters, in step 1433, and adopts such cues, and readies the actions indicated, in step 1435. Similarly, a third party authority, such as the user's dentist, may also request particular treatments and other actions to be undertaken by the oral care device for a particular user, which are communicated to the control system in step 1437. In some instances, it may not be possible to carry out all such treatments and actions requested, as provided in steps 1429 through 1437. In such cases, the control system may deconflict those differing requested treatments and actions, in step 1439. In some such embodiments, deconfliction may be carried out according to rules (e.g., prioritizing a dentist's recommendations for the user over other requests) and carrying out only some of those requests, or prioritizing those requests.

From those deconflicted or otherwise cued actions and treatments of a treatment plan and an action plan, the control system may next select such actions and treatments, and parameters therefor, selecting a duration(s) for operation of the requested oral care treatment(s) and action(s) in step 1441, and particular mode(s) of operation, in step 1443. For example, in some embodiments, the control system may select any of several duration options for carrying out such treatments and actions, in step 1445. As another example, in some embodiments, the control system may select any of several mode or other action options to carry out for the user, in step 1447. The control system may then perform the particular treatments and other actions selected, by issuing actuation commands to actuators within the oral care device, in step 1449. For example, in some embodiments, a "Deep Clean" mode may be selected, in which more vigorous, or longer durations of actuation for brushes, ultrasound and fluid-channeling jets may be performed, and particular treatment fluids, using greater soil removal components (e.g., textured components or surfactants) may be summoned by the control system and implemented. In some embodiments a "Fast" mode may be selected, in which a more superficial, shorter duration actions and treatment are selected and carried out. In some such embodiments, an "on-the-go" sub-mode may be implemented, in which water-retaining seals and fluid recycling and storage techniques set forth in this application may be implemented, such that a user may use the oral care device away from a sink, with no mess (e.g., at his or her desk, or while commuting). As yet another example, in some embodiments, a "Spa" mode may be selected, in which the control system carries out more gentle massaging actions using brushes and ultrasound, with rhythmic, massaging motions, and/or for a longer duration. In some such embodiments, pleasurable-tasting and feeling treatments (such as fluids with essential oils) may be released from jets within oral care device 1300. As yet another example, in some embodiments, a "whitening mode" may be selected, in which whitening treatments are released onto a user's teeth, such as a bleach or deep cleanser, or UV light (from a UV light source within teeth-accepting channels). In some embodiments, any combination of modes or actions and treatments carried out in a particular order, and for particular durations, may be selected for a particular user to carry out any particular treatment recommended for the user.

The control system may then return to the starting position.

Figure 15:
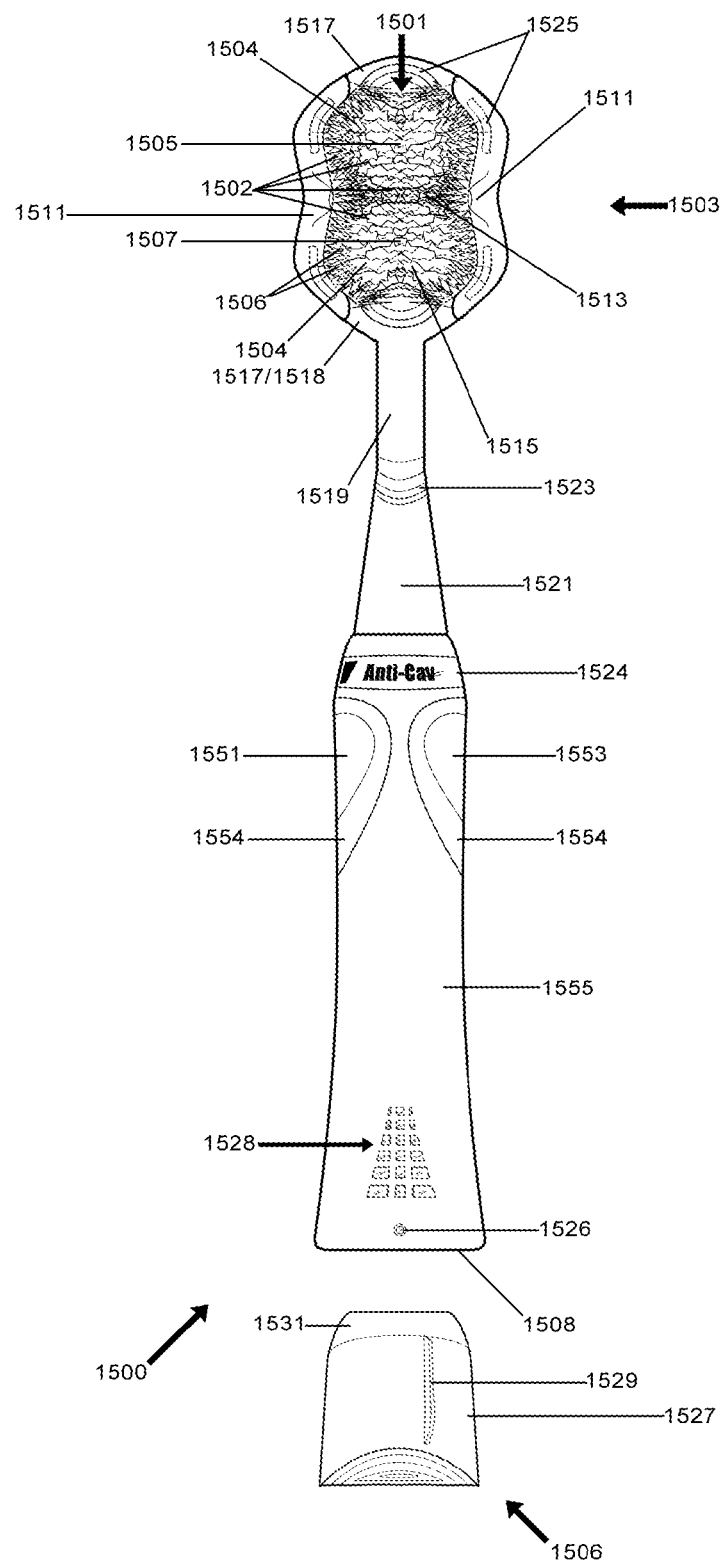
FIG. 15 is a front view of another example oral care device with a more linear format mouthpiece, along with another example cartridge and cartridge-loading compartment.

FIG. 15 is a front view of another example oral care device 1500 with a more linear format mouthpiece 1503, along with an example cartridge 1506 and cartridge-loading compartment 1508, shaped according to another complementary proprietary form factor, and other unique embodiments of the present invention. As with other oral care devices set forth above, in some embodiments, oral care device 1300's mouthpiece, such as the example linear format mouthpiece 1503, includes one or more teeth-accepting channel(s), such as teeth-accepting channel 1501, for accepting one or more teeth in each of an upper and lower set of a user's teeth. In the example pictured, teeth-accepting channel 1501 is shaped to accept two of a user's teeth, in example tooth-accepting pockets 1505 and 1507. To form tooth-accepting pockets 1505 and 1507, teeth-cleaning brush(es) 1502 are provided with complex, tooth-surrounding, curved surfaces, such as the examples shown as curved surfaces 1504, formed by the heads of the bristles, such as example bristles 1506. In some embodiments, those curved surfaces, such as the example shown as example curved surfaces 1504 are curved to conform to, match and/or hug the outer surface curves of a user's teeth and gums. In some embodiments, the contours of the outer surface of tooth-accepting pockets 1505 and 1507 may be created to match a 3-D image or other data of a particular user's teeth, or an average 3-D shape of an average tooth of that particular user. Thus, a user may insert her or his teeth, one each, into tooth-accepting pockets 1505 and 1507, to begin using oral care device 1500 to clean or treat her or his teeth. In some embodiments, and as provided for other oral care devices in the present invention, the control system may sense (e.g., with touch or other pressure sensors connected to bristles 1506), or a camera mounted on mouthpiece 1503) whether a user has so inserted a tooth one each, into each of tooth-accepting pockets 1505 and 1507, and may, in some such embodiments, only perform certain actions (e.g., actuating teeth-cleaning brushes 1502) when the user's teeth are properly inserted into tooth-accepting pockets 1505 and 1507 (e.g., each tooth centered on and seated within each of tooth-accepting pockets 1505 and 1507). Also as with other oral care devices set forth in the present application, in some embodiments, the teeth-cleaning brushes 1502 may be control system-actuable in some embodiments, and each of teeth-cleaning brushes 1502 may be powered and controlled by a control system at least partially within oral care device 1500.

As mentioned above, curved surfaces 1504 may form teeth-accepting pockets, such as tooth-accepting pockets 1505 and 1507. It bears repeating, however, that the recitation of particular orders and numbers of features, such as 1, 2, 3 or some other number of channels, and tooth-accepting pockets, and mouthpieces, with respect to any oral care device set forth in this application, is illustrative of some embodiments, only, and is not in any way limiting as to the scope of the invention.

In any event, if multiple tooth-accepting pockets are provided, as in the example embodiment pictured, interdental cleaning devices may also be provided. As mentioned above such interdental cleaning devices may comprise, or be comprised within, flossing lines or fluid-directing devices, in some embodiments, such as example fluid-releasing port(s) 1511. In some embodiments, such fluid-releasing port(s) 1511 may introduce dentifrice, treatments, water and/or other fluids into teeth-accepting channel 1501, and onto bristles 1506. In some embodiments, such fluid-releasing port(s) may be fluid-ejecting jets, releasing pressurized, or otherwise conditioned streams of fluid (e.g., using an actuator, which may be a motor or an ultrasound actuator in some embodiments.) In some embodiments, curved surfaces 1504, and/or bristles 1506, may also form interdental cleaning devices, such as example interdental-cleaning ridge 1513. In some embodiments, the angle of bristles 1506 may be continuously variable, along the curved surface of 1504. In some such embodiments, the angle of bristles 1506 is so continuously variable to result in closely-matching the surface of a user's teeth and gums when his or her teeth are properly inserted within the tooth-accepting pockets 1505 and 1507. For example, in some such embodiments, the angle of bristles 1506 is so continuously variable according to a function to cause the center tips of each of bristles 1506 to tangentially-touching the user's teeth and/or gums when his or her teeth are properly inserted within the tooth-accepting pockets 1505 and 1507, or approximately so.

In some embodiments, teeth-accepting channel 1501 includes an open-ended, flat trench 1515, with flat open entrances 1517, at each end of the channel. Such an open, flat trench allows fore and aft movement of oral care device, while keeping a line of the user's teeth inserted into the teeth-accepting channel 1501, to aid in manually scrubbing the user's teeth and gums, in some embodiments, and, in some embodiments, allowing a user to quickly reposition teeth accepting channel, and pockets 1505 and 1507, over a different set of teeth, in some embodiments. In some embodiments, the oral care device may provide haptic feedback to the user when she or he has properly inserted two of her teeth into tooth-accepting pockets 1505 and 1507, one each, centered and seated. For example, in some embodiments, the control system issues a distinct vibration to the user, or pattern of vibrations, to indicate that the teeth inserted into tooth-accepting pockets 1505 and 1507 have been properly inserted, and another distinct vibration or pattern of vibrations, when the user's teeth have been adequately cleaned or otherwise treated, and it is time to move oral care device over to a new set of teeth, inserting them into tooth-accepting pockets 1505 and 1507. To ease seating of oral care device 1500 on a user's teeth, in some embodiments, an extended flat section 1519 of a guiding extension 1521 of mouthpiece may be included. In some such embodiments, such an extended flat section 1519 may abut the near flat open entrance 1518, of teeth-accepting channel 1501.

In some embodiments, to aid in maintaining the correct angle of engagement of mouthpiece 1503, while sliding teeth through channel 1501, a swiveling joint 1523 may be provided. In some such embodiments, swiveling joint 1523 may be an omni-directional swivel. In some embodiments, swiveling joint 1523 may be a force-biased swivel, which force-bias forces the return of swiveling joint 1523 to a straightened position, as pictured, in the absence of external forces on swiveling joint 1523.

As with other oral care devices set forth in the present application, a series of user controls and feedback devices may also be included, in some embodiments, which are connected to a control system within (not pictured), or connected to, oral care device 1500. As mentioned above, such a control system may be connected with, and able to issue operational commands to, any and all actuators, displays and sensors set forth in reference to the present figure, or elsewhere in the present application. For example, motors, ultrasonic emitters or other actuators 1525 may be provided in mouthpiece 1503, in some embodiments. In some embodiments, ultrasonic emitters or other actuators 1525 may be provided in a main body 1527, of oral care device 1500.

In some such embodiments, a lighted indicator display 1526 may be provided, and used to indicate particular statuses relevant to the operation of oral care device 1500, such as whether device 1500 has been powered up. In some embodiments, a more complex graphical display, such as example graphical display 1524, may instead, or in addition, be used. In some embodiments, graphical display 1524 may provide a readout indicating a duration of use and a mode of operation, as discussed elsewhere for displays of oral care devices in the present application, and as pictured. For example, in the embodiment pictured, a readout of an "Anti Cavity" mode is indicated, indicating to a user that the oral care device is presently being operated in a mode to encourage the prevention of cavity formation for a user's teeth. For example, in some such embodiments, more fluoride is introduced into channel 1501, than in other modes, and for a longer duration, than in other modes of operation. In some embodiments, a multivariate, touch-actuable, lighted display may be included, such as the example pictured as touch-actuable lighted array display 1528. In some such embodiments, a user may select, and visualize, different parameters of operation of oral care device 1500, for example by touching any surface area of touch-actuable lighted array display 1528, actuating any of its actuable pixels, such as the pixels shown as 1571, causing them to be illuminated and to select a corresponding mode of operation, duration, intensity level, or any other variable parameter of operation. In some embodiments, the higher up the pixels selected, the greater the intensity level of operation indicated and carried out by the oral care device when operated. In some embodiments, the wider the selection of pixels laterally, on either side of touch-actuable lighted array display 1528, the greater the duration, or the greater degree of some mode of operation, is selected and indicated.

As with other oral care devices set forth in this application, in some embodiments, a user may select or request a mode of operation of oral care device 1500 with a mode selection button, such as either of thumb- or finger-actuated mode selection buttons 1551 or 1553. In some embodiments, such thumb- or finger-actuated buttons may be provided within thumb- or finger-grip depressions, such as the examples pictured as 1554. In some embodiments, thumb-grip depressions may comprise biometric or other sensors, to determine whether a user is properly gripping a handle section 1555 of oral care device 1500. In some embodiments, any selections or user-commands required for any mode, intensity or other aspect of the invention may be provided through such user controls.

As mentioned above, in some embodiments, oral care devices in accordance with aspects of the present invention may hold and distribute water, dentifrice, treatments, and other oral care materials from standardized packages, which may be temporarily, reversibly connected to fluid conduits of the oral care devices, to at least part of a user's oral cavity, such as her or his teeth, gums, tongue, sublingual areas, the roof of the mouth, and throat. In some embodiments, such standardized packages may be issued and delivered from a remote source, which may be controlled, at least in part, by a control system and/or a medical authority, such as a dentist. For example, and also as mentioned above, in some embodiments, specialized, standardized cartridges, such as example cartridge 1506, may be so issued. In some embodiments, such standardized packages (e.g., cartridge 1506) may include one or more part(s) with a proprietary format, to ensure that only correct cartridges, approved for use with the particular type of oral care device, are installed onto or into the oral care device. For example, cartridge 1506 is pictured with an unusually-shaped housing 1527, shaped according to a proprietary, unusual form factor—namely, in this example, a generally conical shape of particular proportions, angles and dimensions, with a long tab. As a result, a lateral sliding tab 1529 conforms with that proprietary, unusual form factor. Similarly, a cartridge-loading compartment 1508 is also shaped according to the same, proprietary, unusual form factor, albeit in reverse (bas-relief) to the shape of cartridge 1506, such that cartridge-loading compartment 1508 and cartridge 1506 have a complementary, inverse 3-D form factor relative to one another. As such, and as pictured, cartridge 1506 may be installed into compartment 1508 by sliding end 1531 of cartridge 1506 upward, into cartridge-loading compartment 1508. In some embodiments, cartridge 1506 and oral care device 1500 may include some connectors, which may be conduits, as discussed elsewhere in this application, from an internal tank holding such oral care fluids within cartridge 1506, which deliver fluids to a user's oral cavity. For example, in some embodiments, such conduits within oral care device 1500 connect with ports 1511, delivering fluids from cartridge 1506 to teeth-accepting channel(s) 1501. In some embodiments, such conduits within oral care device 1500 and such conduits from an internal tank of cartridge 1506 may comprise connecting ports, with a complementary form factor for physically interfacing with one another. In some embodiments, such ports include valves which are forced open upon such physical interfacing. In some embodiments, such valves electrical actuators, which are controlled by a control system, which may be present within cartridge 1506 and/or oral care device 1500. For example, in some such embodiments, such a control system may be a control system such as that disclosed in reference to FIG. 10. In some embodiments, multiple such internal tanks may be present in cartridge 1506. In some embodiments, such an internal tank may be present within oral care device 1500. In some such embodiments, of course, cartridges such as 1506 may be omitted, and just such on-board tanks within oral care device 1500, or another source, may, instead, be used. In some such embodiments, such an internal tank may be present within oral care device 1500 and may receive cleaning and treatment fluids from cartridge 1506, which may then be decoupled from oral care device 1500 prior to use.

Similarly, and as with other oral care devices, customized liners with custom-shaped brushes or mouthpieces may be ordered and issued, separately from the remainder of oral care device 1500, in some embodiments. In some such embodiments, such customized liners, brushes and mouthpieces may be optimized for particular modes of operation, or for the cleaning or other treatment needs of a particular user.

In some embodiments, as with other oral care devices discussed in this application, observations may be made by the control system of oral care device 1500, or user operating such a control system, or a control system variably connected with such control system(s). In some such embodiments, sensors are located within mouthpiece 1503, and connected with such a control system. In some such embodiments, such sensors may be a camera. In some such embodiments, such sensors may detect changes in the condition of a user's mouth, at different times, as will be discussed in greater detail below. For example, in some such embodiments, such sensors may detect plaque and/or tooth decay, or any other oral-care relevant conditions, using any technique set forth in the present application for such detection.

Figure 16:
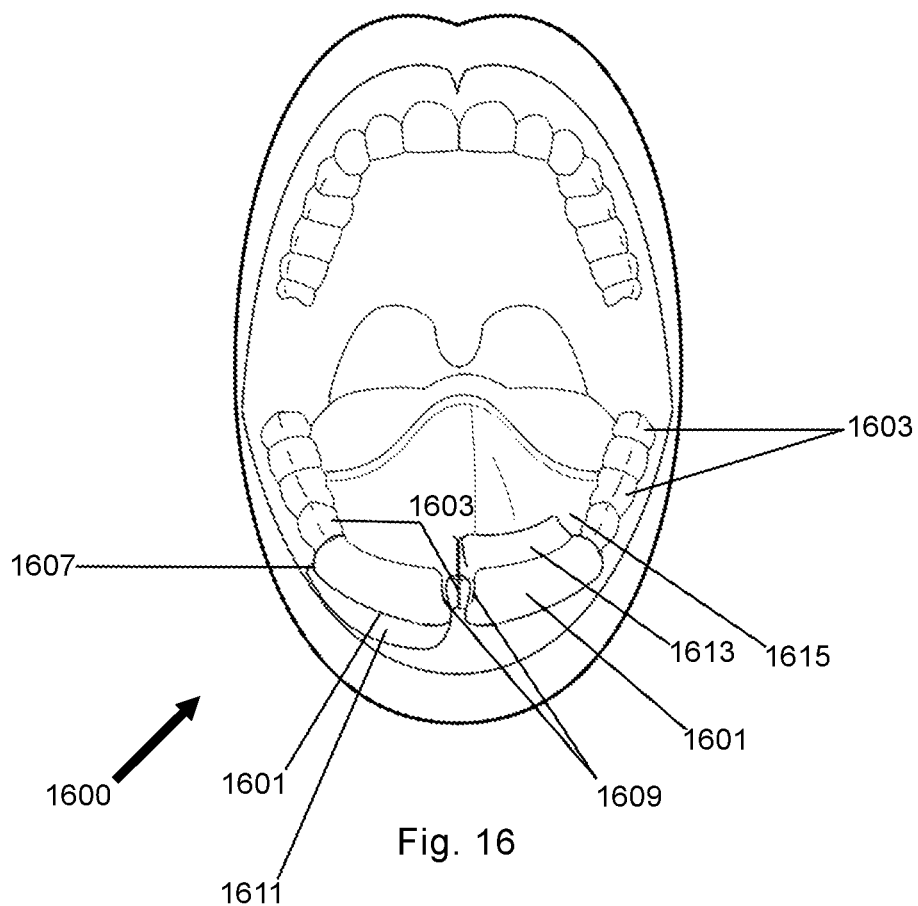
FIG. 16 is a perspective view of an example user's mouth, into which an example oral care device, designed to be entirely contained in the user's mouth when closed (a.k.a., an "in-mouth" oral care device), has been placed at least partially onto, or nearby a user's teeth, in accordance with aspects of the present invention.

FIG. 16 is a perspective view of an example user's mouth 1600, into which an example oral care device 1601, designed to be entirely contained in the user's mouth when closed (a.k.a., an "in-mouth" oral care device), has been placed at least partially onto, or nearby a user's teeth, in accordance with aspects of the present invention. In some embodiments, such an in-mouth oral care device covers at least part of one or more (e.g., two or three, or all, in various embodiments) of the user's teeth, such as example user's teeth 1603.

In various embodiments, oral care device 1601 includes any or all of the aspects of oral care devices set forth elsewhere in this application. For example, in some embodiments, oral care device 1601 includes a control system and actuators, configured to carry out one or more oral care routines, over time. Unlike some oral care devices set forth elsewhere, however, oral care device 1601 has a form factor small enough, and contoured to fit particular internal anatomical features of user's mouth 1600, making oral care device 1601 comfortable over long periods of time, during which it may carry out more gradual, slower routines to enhance the user's oral health. For example, in some embodiments, oral care device 1601 secretes an antimicrobial substance, held within a reservoir within example housing 1607, at a controlled rate, to combat or prevent an oral infection. As another example, in some embodiments, oral care device 1601 similarly secretes a breath-freshening substance, at a controlled rate, to enhance a user's breath. As another example, in some embodiments, oral care device 1601 similarly secretes a teeth-whitening substance, at a controlled rate, to whiten a user's teeth. As another example, in some embodiments, oral care device 1601 similarly secretes an oral analgesic substance, at a controlled rate, to control a user's sensation of pain. As another example, in some embodiments, oral care device 1601 similarly secretes a tooth-fortifying substance, at a controlled rate, to strengthen a user's teeth. As another example, in some embodiments, oral care device 1601 similarly secretes a tooth and/or oral cavity cleaning substance, at a controlled rate, to control a user's sensation of pain. As another example, in some embodiments, oral care device 1601 secretes a drug, vitamin, food, or other health enhancing substance, at a regular, controlled rate according to a doctor's prescription, which substance, in turn, is swallowed or otherwise ingested by the user slowly over time, enhancing the user's health.

In some embodiments, oral care device 1601 may so secrete such substances through ports within example channels 1609. In some embodiments, such channels and/or ports which may be teeth covering, or partially teeth covering, as pictured, and as set forth for teeth-accepting channels set forth elsewhere in this application. In some embodiments, however, such channels and/or ports may also be separate from user's teeth 1603, for example, ejecting fluids onto a user's tongue, oropharynx, or elsewhere within the user's mouth 1600.

Example housing 1607 exhibits a varied form factor, to demonstrate two possible locations and shapes for such a reservoir, such a control system (which may be a control system such as that described with reference to FIG. 10, above) and/or other components of oral care device 1601: Example right-hand side housing section 1611 is located and shaped to fit, at least partially, in a vestibule, next to said user's teeth and lips. Example left-hand side housing section 1613, by contrast, is located and shaped to fit at least partially below the user's tongue, in the sub-lingual area of the user's mouth floor 1615. In either case, owing to its small form factor, and curved shape conforming to a user's internal mouth features, each housing section is comfortable and may go entirely unnoticed by onlookers, because at least the majority of the housing section and oral care device 1601 in general, may be concealed from view (i.e., behind the user's lip(s) or under the user's tongue, respectively). Due to this feature, a user may treat her or his teeth, mouth, or even take an oral medication, in a gradual, metered manner, over a long period of time than with ordinary brushing, mouthwashing, or drug dosage regimes. In some embodiments, any of the housings above may include a flexible, compliant material (e.g., rubber or silicone), to further enhance the user's comfort.

Although the example of in-mouth oral care device 1601 is shown as place on or about the user's lower set of teeth, and, specifically, at least some of her front, lower teeth, it should, of course, be understood that in-mouth oral care device 1601 may be placed elsewhere, such as over some of the user's upper teeth and/or back teeth, and between the lip and teeth or gums or toward the center of her oral cavity, having a shape that conforms to any of those areas of her mouth, as the case may be. The examples provided are, of course, only examples of the virtually unlimited locations and form factors falling within the scope of the present application, as with all other figures and examples set forth herein.

I claim:

1. An oral care device comprising:
    a set of at least one channel(s) configured to accept at least two of a user's teeth;
    wherein said set of at least one channel(s) comprises at least one fluid-passing port(s) configured to pass fluid(s) onto and/or between said at least two of a user's teeth;
    a control system, comprising a power source and actuator(s);
    at least one brush(es) located at least partially within said channel(s), configured to be driven by said actuator(s); and wherein said control system is configured to actuate said actuators based on a user-issued command.

2. The oral care device of claim 1, wherein the user-issued command comprises a user biting into said at least one channel(s), which is sensed by the control system.

3. The oral care device of claim 1, wherein the user-issued command comprises a user touching a switch, button or touch-sensitive control on the outer surface of said oral care device.

4. The oral care device of claim 3, wherein the switch, button or touch-sensitive control is located on an outer surface of the oral care device, and wherein the outer surface faces, and is accessible and actuable by, the user's tongue when the oral device is at least partially mounted on or about a user's teeth.

5. The oral care device of claim 1, wherein the user-issued command comprises a user issuing an electromagnetic signal to the oral care device, via a device remote from said oral care device; and
 wherein said device remote from said oral care device comprises specialized computer hardware and software.

6. The oral care device of claim 5, wherein the device remote from said oral care device is a smartphone or other form of personal digital device.

7. The oral care device of claim 1, wherein said fluid-passing port(s) send stream(s) of said fluid(s) in pulses when passing said fluid(s).

8. The oral care device of claim 1, wherein said oral care device comprises an ultrasound actuator, creating vibrations to clean said user's teeth.

9. The oral care device of claim 1, wherein said oral care device carries out a set of actions to clean and/or otherwise treat said user's teeth.

10. The oral care device of claim 9, wherein said oral care device is configured to be operated in one or more of a plurality of modes of operation and/or a combination of said one or more of a plurality of modes of operation, and wherein said set of actions is created, at least in part, based on said one or more of a plurality of modes of operation.

11. The oral care device of claim 10, wherein an intensity and/or a duration of said actions are defined by said one or more of a plurality of modes of operation.

12. The oral care device of claim 1, comprising a cartridge-loading compartment, comprising a communications interface for accepting commands and/or data from a cartridge.

13. The oral care device of claim 12, wherein said cartridge-loading compartment is configured to receive one or more cartridge(s) comprising at least some of said fluid(s), and wherein said oral care device is configured to receive said at least some of said fluid(s) from said cartridge(s) and distribute said fluids to one or more of said at least one channel(s).

14. The oral care device of claim 1, wherein said at least one channel(s) comprise two channels.

15. The oral care device of claim 1, wherein said at least one channel(s) are custom-fit to said user's mouth, based on a 3-D impression, scan or image of said user's mouth.

16. An oral care device comprising:
 a set of at least one channel(s) configured to cover at least part of two of a user's teeth;
 wherein said set of at least one channel(s) comprises at least one fluid-passing port(s) configured to pass fluid(s) onto and/or between said at least two of said user's teeth;
 a control system, comprising a power source and controlling actuator(s);
 at least one teeth-cleaning and/or treating actuator, comprised in said actuator(s), located at least partially within said at least one channel(s).

17. The oral care device of claim 16, wherein the oral care device is configured to sit on a floor of said user's mouth, at least partially below his or her tongue, when properly placed onto said user's teeth.

18. The oral care device of claim 16, wherein the oral care device is configured to sit, at least partially, in a vestibule, next to said user's teeth.

19. The oral care device of claim 16, wherein said at least one channel(s) are custom-fit to a particular user's mouth, based on a 3-D impression, scan or image of said user's mouth.

20. The oral care device of claim 16, wherein at least part of said oral care device is custom-fit to a particular user's mouth, based on a 3-D impression, scan and/or image of said user's mouth.

* * * * *